US008298757B2

(12) United States Patent
Takahashi et al.

(10) Patent No.: US 8,298,757 B2
(45) Date of Patent: Oct. 30, 2012

(54) RAPID DIAGNOSIS METHOD SPECIFIC TO AVIAN INFLUENZA VIRUS

(75) Inventors: Kazuo Takahashi, Osaka (JP); Yoshinobu Okuno, Osaka (JP); Hiroshi Nishimura, Osaka (JP); Takeshi Imoarai, Kobe (JP); Noriyuki Saito, Kobe (JP); Tomokuni Taniguchi, Kobe (JP)

(73) Assignees: Osaka Prefectural Government, Osaka (JP); Sysmex Corporation, Hyogo (JP)

( * ) Notice: Subject to any disclaimer, the term of this patent is extended or adjusted under 35 U.S.C. 154(b) by 555 days.

(21) Appl. No.: 12/439,432

(22) PCT Filed: Aug. 31, 2007

(86) PCT No.: PCT/JP2007/067072

§ 371 (c)(1), (2), (4) Date: Jul. 20, 2009

(87) PCT Pub. No.: WO2008/026741

PCT Pub. Date: Mar. 6, 2008

(65) Prior Publication Data

US 2009/0311667 A1 Dec. 17, 2009

(30) Foreign Application Priority Data

Aug. 31, 2006 (JP) ................................ 2006-235356
Jan. 29, 2007 (JP) ................................ 2007-018400

(51) Int. Cl.
*C12Q 1/70* (2006.01)
*C07K 16/08* (2006.01)

(52) U.S. Cl. ...... 435/5; 435/7.1; 530/388.3; 530/388.85

(58) Field of Classification Search ........................ None
See application file for complete search history.

(56) References Cited

U.S. PATENT DOCUMENTS

2006/0105328 A1 5/2006 Lu

FOREIGN PATENT DOCUMENTS

JP 2006-067979 A 3/2006
WO 2005/007697 A1 1/2005

OTHER PUBLICATIONS

Bai et al., J Vet Med Sci 2006 vol. 68, pp. 35-40.*
Liu et al., Chin J Cell Mol Immunol 2006 vol. 22, pages starting 648 (3 pages).*
Wong et al.; "Avian Influenza Virus Infections in Humans"; Chest; c. Jan. 2006; pp. 156-168; vol. 129; American College of Chest Physicians; Global Medicine.
Fedorko et al.; "Performance of Rapid Tests for Detection of Avian Influenza A Virus Types H5N1 and H9N2"; Journal of Clinical Microbiology; c. Apr. 2006; pp. 1596-1597; vol. 4, No. 4.
Zhang et al.; "Development and Evaluation of DAS-ELISA for Rapid Detection of Avian Influenza Viruses"; Avian Diseases; American Association of Avian Pathologists; c. Sep. 2006; pp. 325-330; vol. 50, No. 3; USA.

* cited by examiner

*Primary Examiner* — Mary E Mosher
*Assistant Examiner* — Myron Hill
(74) *Attorney, Agent, or Firm* — Sughrue Mion, PLLC

(57) ABSTRACT

The present invention relates to a method for detecting an avian influenza virus by an immunological assay using an anti-influenza virus antibody being unreactive to human influenza type-A virus subtypes H1, H2 and H3 and a human influenza type-B virus and being reactive to plural subtypes of avian influenza viruses, and an immunochromatographic test tool for use in the method. According to the present invention, an avian influenza virus can be detected specifically, rapidly and in a simple manner, as distinguishing an avian influenza virus from a human influenza virus.

10 Claims, 14 Drawing Sheets

Figure 4

| | | |
|---|---|---|
| A/Duck/Australia/341/83_H15N8_ | MASQGTKRSYEQMETGGERQNATEIRASVGRMVGGIGRFYIQMCTELKLN | 50 |
| A/Mallard/Astrakan/263/82_H14N8_ | MASQGTKRSYEQMETGGERQNATEIRASVGRMVGGIGRFYIQMCTELKLS | 50 |
| A/gull/Maryland/704/1977_H13N6_ | MASQGTKRSYEQMETGGDRQNANEIRASVGRMVGGIGRFYIQMCTELKLS | 50 |
| A/pintail/Alberta/49/2003_H12N5_ | MASQGTKRSYEQMETGGERQNATEIRASVGRMVGGIGRFYIQMCTELKLS | 50 |
| A/duck/England/1956_H11N6_ | MASQGTKRSYEQMETGGERQNATEIRASVGRMVGGIGRFYIQMCTELKLS | 50 |
| A/pintailduck/ALB/584/1984_H10N6_ | MASQGTKRSYEQMETGGERQNATEIRASVGRMVGGIGRFYIQMCTELKLS | 50 |
| A/shorebird/DE/261/2003_H9N5_ | MASQGTKRSYEQMETGGERQNATEIRASVGRMVGGIGRFYIQMCTELKLS | 50 |
| A/turkey/Ontario/6118/1968_H8N4_ | MASQGTKRSYEQMETGGERQNATEIRASVGRMVGGIGRFYIQMCTELKLS | 50 |
| A/chicken/Germany/R28/03_H7N7_ | MASQGTKRSYEQMETGGERQNATEIRASVGRMVGGIGRFYIQMCTELKLS | 50 |
| A/shearwater/Australia/1972_H6N5_ | MASQGTKRSYEQMETGGERQNATEIRASVGRMVGGIGRFYIQMCTELKLS | 50 |
| A/blackduck/NewYork/184/1988_H5N2_ | MASQGTKRSYEQMETGGERQNATEIRASVGRMVGGIGRFYIQMCTELKLS | 50 |
| A/turkey/Ontario/7732/1966_H5N9_ | MASQGTKRSYEQMETGGERQNATEIRASVGRMVGGIGRFYIQMCTELKLS | 50 |
| r-Avian Flu NP | MASQGTKRSYEQMETGGERQNATEIRASVGRMVGGIGRFYIQMCTELKLS | 50 |
| A/HongKong/117/1977_H1N1_ | MASQGTKRSYEQMETDGERPNATEIRASVGKMIDGIGRFYIQMCTELKLS | 50 |
| A/Japan/170/62_H2N2_ | MASQGTKRSYEQMETDGERQNATEIRASVGKMIDGIGRFYIQMCTELKLS | 50 |
| A/Kitakyushu/159/93_H3N2_ | MASQGTKRSYEQMETDGERQNATEIRASVGKMIDGIGRFYIQMCTELKLS | 50 |
| A/Kumamoto/1/65_H2N2_ | MASQGTKRSYEQMETDGERQNATEIRASVGKMIDGIGRFYIQMCTELKLS | 50 |
| A/NewYork/5/2004_H3N2_ | MASQGTKRSYEQMETDGDRQNATEIRSSVGKMIDGIGRFYIQMCTELKLS | 50 |
| A/PuertoRico/8/34_H1N1_ | MASQGTKRSYEQMETDGERQNATEIRASVGKMIGGIGRFYIQMCTELKLS | 50 |
| A/Kiev/59/79_H1N1_ | MASQGTKRSYEQMETDGERQNATEIRASVGKMIDGIGRFYIQMCTELKLS | 50 |
| A/Beijing/353/1989_H3N2_ | MASQGTKRSYEQMETDGERQNATEIRASVGKMIDGIGRFYIQMCTELKLS | 50 |
| A/Brazil/11/1978_H1N1_ | MASQGTKRSYEQMETDGERQNATEIRASVGKMIDGIGRFYIQMCTELKLS | 50 |
| A/Victoria/15681/59_H2N2_ | MAFQGTKRSYEQMETDGERQNATEIRASVGKMIDGIGRFYIQMCTELKLS | 50 |
| A/NewCaledonia/20/1999_H1N1_ | MASQGTKRSYEQMETDGERQNATEIRASVGRMIGGIGRFYIQMCTELKLN | 50 |
| A/Panama/2007/1999_H3N2_ | MASQGTKRSYEQMETDGDRQNATEIRASVGKMIDGIGRFYIQMCTELKLS | 50 |
| r-Human Flu NP | MASQGTKRSYEQMETDGERQNATEIRASVGKMIGGIGRFYIQMCTELKLS | 50 |

Figure 5

| | | |
|---|---|---|
| A/Duck/Australia/341/83_H15N8_ | DHEGRLIQNSITIERMVLSAFDERRNKYLEEHPSTGKDPKKTGGPIYRRR | 100 |
| A/Mallard/Astrakan/263/82_H14N8_ | DYEGRLIQNSITIERMVLSAFDERRNKYLEEHPSAGKDPKKTGGPIYRRR | 100 |
| A/gull/Maryland/704/1977_H13N6_ | DNEGRLIQNSITIERMVLSAFDERRNKYLEEHPSTGRDPKKTGGPIYRRR | 100 |
| A/pintail/Alberta/49/2003_H12N5_ | DYEGRLIQNSITIERMVLSAFDERRNKYLEEHPSAGKDPKKTGGPIYRRR | 100 |
| A/duck/England/1956_H11N6_ | DYEGRLIQNSITIERMVLSAFDERRNKYLEEHPSAGKDPKKTGGPIYRRR | 100 |
| A/pintailduck/ALB/584/1984_H10N6_ | DYEGRLIQNSITIERMVLSAFDERRNKYLEEHPSAGKDPKKTGGPIYRRR | 100 |
| A/shorebird/DE/261/2003_H9N5_ | DYEGRLIQNSITIERMVLSAFDERRNKYLEEHPSAGKDPKKTGGPIYRRR | 100 |
| A/turkey/Ontario/6118/1968_H8N4_ | DYEGRLIQNSITIERMVLSAFDERRNKYLEEHPSAGKDPKKTGGPIYRRR | 100 |
| A/chicken/Germany/R28/03_H7N7_ | DHEGRLIQNSITIERMVLSAFDERRNKYLEEHPSAGKDPKKTGGPIYRRR | 100 |
| A/shearwater/Australia/1972_H6N5_ | DHEGRLIQNSITIERMVLSAFDERRNKYLEEHPSAGKDPKKTGGPIYRRR | 100 |
| A/blackduck/NewYork/184/1988_H5N2_ | DYEGRLIQNSITIERMVLSAFDERRNKYLEEHPSAGKDPKKTGGPIYRRR | 100 |
| A/turkey/Ontario/7732/1966_H5N9_ | DYEGRLIQNSITIERMVLSAFDERRNKYLEEHPSAGKDPKKTGGPIYRRR | 100 |
| r-Avian Flu NP | DYEGRLIQNSITIERMVLSAFDERRNKYLEEHPSAGKDPKKTGGPIYRRR | 100 |
| A/HongKong/117/1977_H1N1_ | DYEGRLIQNSLTIERMVLSAFDERRNKYLEEHPSAGKDPKKTGGPIYKRV | 100 |
| A/Japan/170/62_H2N2_ | DYEGRLIQNSLTIERMVLSAFDERRNKYLEEHPSAGKDPKKTGGPIYKRV | 100 |
| A/Kitakyushu/159/93_H3N2_ | DYEGRLIQNSLTIERMVLSAFDERRNRYLEEHPSAGKDPKKTGGPIYKRV | 100 |
| A/Kumamoto/1/65_H2N2_ | DYEGRLIQNSLTIERMVLSAFDERRNKYLEEHPSAGKDPKKTGGPIYKRV | 100 |
| A/NewYork/5/2004_H3N2_ | DYEGRLIQNSLTIEKMVLSAFDERRNRYLEEHPSAGKDPKKTGGPIYKRV | 100 |
| A/PuertoRico/8/34_H1N1_ | DYEGRLIQNSLTIERMVLSAFDERRNKYLEEHPSAGKDPKKTGGPIYRRV | 100 |
| A/Kiev/59/79_H1N1_ | DYEGRLIQNSLTIERMVLSAFDERRNRYLEEHPSAGKDPKKTGGPIYKRV | 100 |
| A/Beijing/353/1989_H3N2_ | DYEGRLIQNSLTIERMVLSAFDERRNRYLEEHPSAGKDPKKTGGPIYKRV | 100 |
| A/Brazil/11/1978_H1N1_ | DYEGRLIQNSLTIERMVLSAFDERRNKYLEEHPSAGKDPKKTGGPIYKRV | 100 |
| A/Victoria/15681/59_H2N2_ | DYEGRLIQNSLTIERMVLSAFDERRNKYLEEHPSAGKDPKKTGGPIYKRV | 100 |
| A/NewCaledonia/20/1999_H1N1_ | DYEGRLIQNSLTIERMVLSAFDERRNKYLEEHPSAGKDPKKTGGPIYKRV | 100 |
| A/Panama/2007/1999_H3N2_ | DYEGRLIQNSLTIEKMVLSAFDERRNRYLEEHPSAGKDPKKTGGPIYRRV | 100 |
| r-Human Flu NP | DYEGRLIQNSLTIERMVLSAFDERRNKYLEEHPSAGKDPKKTGGPIYRRV | 100 |

Figure 6

| | | |
|---|---|---|
| A/Duck/Australia/341/83_H15N8_ | DGKWMRELILYDKDEIRRIWRQANNGDDATAGLTHLMIWHSNLNDATYQR | 150 |
| A/Mallard/Astrakan/263/82_H14N8_ | DGKWMRELILYDKEEIRRIWRQANNGEDATAGLTHLMIWHSNLNDATYQR | 150 |
| A/gull/Maryland/704/1977_H13N6_ | DGKWVRELVLYDKEEIRRIWRQANNGEDATAGLTHLMIWHSNLNDATYQR | 150 |
| A/pintail/Alberta/49/2003_H12N5_ | DGKWMRELILYDKEEIRRIWRQANNGEDATAGLTHLMIWHSNLNDATYQR | 150 |
| A/duck/England/1956_H11N6_ | DGKWVRELILYDKEEIRRIWRQANNGEDATAGLTHLMIWHSNLNDATYQR | 150 |
| A/pintailduck/ALB/584/1984_H10N6_ | DGKWMRELILYDKEEIRRIWRQANNGEDATAGLTHLMIWHSNLNDATYQR | 150 |
| A/shorebird/DE/261/2003_H9N5_ | DGKWMRELILYDKEEIRRIWRQANNGEDATAGITHLMIWHSNLNDATYQR | 150 |
| A/turkey/Ontario/6118/1968_H8N4_ | DGKWVRELTLYDKEEIRRIWRQANNGEDATAGLTHLMIWHSNLNDATYQR | 150 |
| A/chicken/Germany/R28/03_H7N7_ | DGKWMRELILYDKEEIRRIWRQANNGEDATAGLTHLMIWHSNLNDATYQR | 150 |
| A/shearwater/Australia/1972_H6N5_ | DGKWMRELILYDKEEIRRIWRQRNNGDDATAGLTHLMIWHSNLNDATYQR | 150 |
| A/blackduck/NewYork/184/1988_H5N2_ | DGKWMRELILYDKEEIRRIWRQANNGEDATAGLTHLMIWHSNLNDATYQR | 150 |
| A/turkey/Ontario/7732/1966_H5N9_ | DGKWMRELILYDKEEIRRIWRQANNGENAAAGLTHLMIWHSNLNDATYQR | 150 |
| r-Avian Flu NP | DGKWMRELILYDKEEIRRIWRQANNGENAAAGLTHLMIWHSNLNDATYQR | 150 |
| A/HongKong/117/1977_H1N1_ | DGKWMRELVLYDKEEIRRIWRQANNGDDATAGLTHMMIWHSNLNDTTYQR | 150 |
| A/Japan/170/62_H2N2_ | NGKWMRELVLYDKEEIRRIWRQANNGDDATAGLTHMMIWHSNLNDTTYQR | 150 |
| A/Kitakyushu/159/93_H3N2_ | DGRWMRELVLYDKEEIRRIWRQANNGDDATAGLTHMMIWHSNLNDTTYQR | 150 |
| A/Kumamoto/1/65_H2N2_ | DRKWMRELVLYDKEEIRRIWRQANNGDDATAGLTHMMIWHSNLNDTTYQR | 150 |
| A/NewYork/5/2004_H3N2_ | DGRWMRELVLYDKEEIRRIWRQANNGEDATAGLTHMMIWHSNLNDATYQR | 150 |
| A/PuertoRico/8/34_H1N1_ | NGKWMRELILYDKEEIRRIWRQANNGDDATAGLTHMMIWHSNLNDATYQR | 150 |
| A/Kiev/59/79_H1N1_ | DRKWMRELILYDKEEIRRIWRQANNGDDATAGLTHMMIWHSNLNDTTYQR | 150 |
| A/Beijing/353/1989_H3N2_ | NGRWMRELVLYDKEEIRRIWRQANNGDDATAGLTHMMIWHSNLNDTTYQR | 150 |
| A/Brazil/11/1978_H1N1_ | DGKWMRELVLYDKEEIRRIWRQANNGDDATAGLTHMMIWHSNLNDTTYQR | 150 |
| A/Victoria/15681/59_H2N2_ | NGKWMRELVLYDKEEIRRIWRQANNGDDATAGLTHMMIWHSNLNDTTYQR | 150 |
| A/NewCaledonia/20/1999_H1N1_ | DGKWVRELVLYDKEEIRRIWRQANNGDDATAGLTHIMIWHSNLNDTTYQR | 150 |
| A/Panama/2007/1999_H3N2_ | DGKWMRELVLYDKEEIRRIWRQANNGEDATAGLTHMMIWHSNLNDTTYQR | 150 |
| r-Human Flu NP | NGKWMRELILYDKEEIRRIWRQANNGDDATAGLTHMMIWHSNLNDATYQR | 150 |

Figure 7

| | | |
|---|---|---|
| A/Duck/Australia/341/83_H15N8_ | TRALVRTGMDPRMCSLMQGSTLPRRSGAAGAAVKGVGTMAMELIRMIKRG | 200 |
| A/Mallard/Astrakan/263/82_H14N8_ | TRALVRTGMDPRMCSLMQGSTLPRRSGAAGAAVKGVGTMVMELIRMIKRG | 200 |
| A/gull/Maryland/704/1977_H13N6_ | TRALVRTGMDPRMCSLMQGSTLPRRSGAAGAAVKGVGTMVMELIRMIKRG | 200 |
| A/pintail/Alberta/49/2003_H12N5_ | TRALVRTGMDPRMCSLMQGSTLPRRSGAAGAAVKGVGTMVMELIRMIKRG | 200 |
| A/duck/England/1956_H11N6_ | TRALVRTGMDPRMCSLMQGSTLPRRSGAAGAAVKGVGTMIMELIRMIKRG | 200 |
| A/pintailduck/ALB/584/1984_H10N6_ | TRALVRTGMDPRMCSLMQGSTLPRRSGAAGAAVKGVGTMVMELIRMIKRG | 200 |
| A/shorebird/DE/261/2003_H9N5_ | TRALVRTGMDPRMCSLMQGSTLPRRSGAAGAAVKGVGTMVMELIRMIKRG | 200 |
| A/turkey/Ontario/6118/1968_H8N4_ | TRALVRTGMDPRMCSLMQGSTLPRRSGAAGAAVKGVGTMVMELIRMIKRG | 200 |
| A/chicken/Germany/R28/03_H7N7_ | TRALVRTGMDPRMCSLMQGSTLPRRSGAAGAAVKGVGTMVMELIRMIKRG | 200 |
| A/shearwater/Australia/1972_H6N5_ | TRALVRTGMDPRMCSLMQGSTLPRRSGAAGAAVKGVGTMVMELIRMIKRG | 200 |
| A/blackduck/NewYork/184/1988_H5N2_ | TRALVRTGMDPRMCSLMQGSTLPRRSGAAGAAVKGVGTMVMELIRMIKRG | 200 |
| A/turkey/Ontario/7732/1966_H5N9_ | TRALVRTGMDPRMCSLMQGSTLPRRSGAAGAAVKGVGTMVMELIRMIKRG | 200 |
| r-Avian Flu NP | TRALVRTGMDPRMCSLMQGSTLPRRSGAAGAAVKGVGTMVMELIRMIKRG | 200 |
| A/HongKong/117/1977_H1N1_ | TRALVRTGMDPRMCSLMQGSTLPRRSGAAGAAVKGVGTMVLELIRMIKRG | 200 |
| A/Japan/170/62_H2N2_ | TRALVRTGMDPRMCSLMQGSTLPRRSGAAGAAVKGVGTMVMELIRMIKRG | 200 |
| A/Kitakyushu/159/93_H3N2_ | TRALVRTGMDPRMCSLMQGSTLPRRSGAAGAAVKGIGTMVMELIRMIKRG | 200 |
| A/Kumamoto/1/65_H2N2_ | TRALVRTGMDPRMCSLMQGSTLPRRSGAAGAAVKGVGTMVMELIRMIKRG | 200 |
| A/NewYork/5/2004_H3N2_ | TRALVRTGMDPRMCSLMQGSTLPRRSGAAGAAVKGIGTMVMELIRMIKRG | 200 |
| A/PuertoRico/8/34_H1N1_ | TRALVRTGMDPRMCSLMQGSTLPRRSGAAGAAVKGVGTMVMELVRMIKRG | 200 |
| A/Kiev/59/79_H1N1_ | TRALVRTGMDPRMCSLMQGSTLPRRSGAAGAAVKGVGTMVMELIRMIKRG | 200 |
| A/Beijing/353/1989_H3N2_ | TRALVRTGMDPRMCSLMQGSTLPRRSGAAGAAVKGIGTMVMELIRMIKRG | 200 |
| A/Brazil/11/1978_H1N1_ | TRALVRTGMDPRMCSLMQGSTLPRRSGAAGAAVKGVGTMVLELIRIIKRG | 200 |
| A/Victoria/15681/59_H2N2_ | TRALVRTGMDPRMCSLMQGSTLPRRSGAAGAAVKGVGTMVMELIRMIKRG | 200 |
| A/NewCaledonia/20/1999_H1N1_ | TRALVRTGMDPRMCSLMQGSTLPRRSGAAGAAVKGVGTMVLELIRMIKRG | 200 |
| A/Panama/2007/1999_H3N2_ | TRALVRTGMDPRMCSLMQGSTLPRRSGAAGAAVKGIGTMVMELIRMVKRG | 200 |
| r-Human Flu NP | TRALVRTGMDPRMCSLMQGSTLPRRSGAAGAAVKGVGTMVMELIRMIKRG | 200 |

Figure 8

| | | |
|---|---|---|
| A/Duck/Australia/341/83_H15N8_ | INDRNFWRGENGRRTRIAYERMCNILKGKFQTAAQRAMMDQVRESRNPGN | 250 |
| A/Mallard/Astrakan/263/82_H14N8_ | INDRNFWRGENGRRTRIAYERMCNILKGKFQTAAQRAMMDQVRESRNPGN | 250 |
| A/gull/Maryland/704/1977_H13N6_ | VNDRNFWRGENGRRTRIAYERMCNILKGKFQTAAQRAMMDQVRESRNPGN | 250 |
| A/pintail/Alberta/49/2003_H12N5_ | INDRNFWRGENGRRTRIAYERMCNILKGKFQTAAQRAMMDQVRESRNPGN | 250 |
| A/duck/England/1956_H11N6_ | INDRNFWRGENGRRTRIAYERMCNILKGKFQTAAQRAMMDQVRESRNPGN | 250 |
| A/pintailduck/ALB/584/1984_H10N6_ | INDRNFWRGENGRRTRIAYERMCNILKGKFQTAAQRAMMDQVRESRNPGN | 250 |
| A/shorebird/DE/261/2003_H9N5_ | VNDRNFWRGENGRRTRIAYERMCNILKGKFQTAAQRAMMDQVRESRNPGN | 250 |
| A/turkey/Ontario/6118/1968_H8N4_ | INDRNFWRGENGRRTRIAYERMCNILKGKFQTAAQRAMMDQVRESRNPGN | 250 |
| A/chicken/Germany/R28/03_H7N7_ | INDRNFWRGENGRRTRIAYERMCNILKGKFQTAAQRAMMDQVRESRNPGN | 250 |
| A/shearwater/Australia/1972_H6N5_ | INDRNFWRGENGRRTRIAYERMCNILKGKFQTAAQRAMMDQVRESRNPGN | 250 |
| A/blackduck/NewYork/184/1988_H5N2_ | INDRNFWRGENGRRTRIAYERMCNILKGKFQTAAQRAMMDQVRESRNPGN | 250 |
| A/turkey/Ontario/7732/1966_H5N9_ | INDRNFWRGENGRRTRIAYERMCNILKGKFQTAAQRAMMDQVRESRNPGN | 250 |
| r-Avian Flu NP | INDRNFWRGENGRRTRIAYERMCNILKGKFQTAAQRAMMDQVRESRNPGN | 250 |
| A/HongKong/117/1977_H1N1_ | INDRNFWRGENGRKTRIAYERMCNILKGKFQTAAQRAMMDQVRESRNPGN | 250 |
| A/Japan/170/62_H2N2_ | INDRNFWRGENGRKTRNAYERMCNILKGKFQTAAQRAMMDQVRESRNPGN | 250 |
| A/Kitakyushu/159/93_H3N2_ | INDRNFWRGENGRKTRSAYERMCNILKGKFQTAAQRAMMDQVRESRNPGN | 250 |
| A/Kumamoto/1/65_H2N2_ | INDRNFWRGENGRKTRSAYERMCNILKGKFQTAAQRAMMDQVRESRNPGN | 250 |
| A/NewYork/5/2004_H3N2_ | INDRNFWRGENGRKTRSAYERMCNILKGKFQTAAQRAMVDQVRESRNPGN | 250 |
| A/PuertoRico/8/34_H1N1_ | INDRNFWRGENGRKTRIAYERMCNILKGKFQTAAQKAMMDQVRESRNPGN | 250 |
| A/Kiev/59/79_H1N1_ | INDRNFWRGENGRKTRSAYERMCNILKGKFQTAAQRAMMDQVRESRNPGN | 250 |
| A/Beijing/353/1989_H3N2_ | INDRNFWRGENGRKTRSAYERMCNILKGKFQTAAQRAMMDQVRESRNPGN | 250 |
| A/Brazil/11/1978_H1N1_ | INDRNFWRGENGRKTRIAYERMCNILKGKFQTAAQRAMMDQVRESRNPGN | 250 |
| A/Victoria/15681/59_H2N2_ | INDRNFWRGENGRKTRNAYERMCNILKGKFQTAAQRAMMDQVRESRNPGN | 250 |
| A/NewCaledonia/20/1999_H1N1_ | INDRNFWRGENGRKTRIAYERMCNILKGKFQTAAQKAMMDQVRESRNPGN | 250 |
| A/Panama/2007/1999_H3N2_ | INDRNFWRGENGRKTRSAYERMCNILKGKFQTAAQRAMVDQVRESRNPGN | 250 |
| r-Human Flu NP | INDRNFWRGENGRKTRIAYERMCNILKGKFQTAAQKAMMDQVRESRNPGN | 250 |

Figure 9

| | | |
|---|---|---|
| A/Duck/Australia/341/83_H15N8_ | AEIEDLIFLARSALILRGSVAHKSCLPACVYGLAVANGHDFEREGYSLVG | 300 |
| A/Mallard/Astrakan/263/82_H14N8_ | AEIEDLIFLARSALILRGSVAHKSCLPACVYGLAVASGYDFEREGYSLVG | 300 |
| A/gull/Maryland/704/1977_H13N6_ | AEIEDLIFLARSALILRGAVAHKSCLPACVYGLAVASGYDFEREGYSLVG | 300 |
| A/pintail/Alberta/49/2003_H12N5_ | AEIEDLIFLARSALILRGSVAHKSCLPACVYGLAVASGYDFEREGYSLVG | 300 |
| A/duck/England/1956_H11N6_ | AEIEDLIFLARSALILRGSVAHKSCLPACVYGLAVASGYDFEREGYSLVG | 300 |
| A/pintailduck/ALB/584/1984_H10N6_ | AEIEDLIFLARSALILRGSVAHKSCLPACVYGLAVASGYDFEREGYSLVG | 300 |
| A/shorebird/DE/261/2003_H9N5_ | AEIEDLIFLARSALILRGSVAHKSCLPACVYGLAVASGYDFEREGYSLVG | 300 |
| A/turkey/Ontario/6118/1968_H8N4_ | AEIEDLIFLARSALILRGSVAHKSCLPACVYGLAVASGYDFEREGYSLVG | 300 |
| A/chicken/Germany/R28/03_H7N7_ | AEIEDLIFLARSALILRGSVAHKSCLPACVYGLAVASGYDFEREGYSLVG | 300 |
| A/shearwater/Australia/1972_H6N5_ | AEIEDLIFLARSALILRGSVAHKSCLPACVYGLAVAGGYDFEREGYSLVG | 300 |
| A/blackduck/NewYork/184/1988_H5N2_ | AEIEDLIFLARSALILRGSVAHKSCLPACVYGLAVASGYDFEREGYSLVG | 300 |
| A/turkey/Ontario/7732/1966_H5N9_ | AEIEDLIFLARSALILRGSVAHKSCLPACVYGLAVASGYDFEREGYSLVG | 300 |
| r-Avian Flu NP | AEIEDLIFLARSALILRGSVAHKSCLPACVYGLAVASGYDFEREGYSLVG | 300 |
| A/HongKong/117/1977_H1N1_ | AEIEDLIFLARSALILRGSVAHKSCLPACVYGPAVASGYDFEKEGYSLVG | 300 |
| A/Japan/170/62_H2N2_ | AEIEDLIFLARSALILRGSVAHKSCLPACVYGPAVASGYDFEKEGYSLVG | 300 |
| A/Kitakyushu/159/93_H3N2_ | AEIEDLIFSARSALILRGSVAHKSCLPACVYGPAVSSGYNFEKEGYSLVG | 300 |
| A/Kumamoto/1/65_H2N2_ | AEIEDLIFLARSALILRGSVAHKSCLPACVYGPAVASGYDFEKEGYSLVG | 300 |
| A/NewYork/5/2004_H3N2_ | AEIEDLIFLARSALILRGSVAHKSCLPACVYGPAVSSGYDFEKEGYSLVG | 300 |
| A/PuertoRico/8/34_H1N1_ | AEFEDLTFLARSALILRGSVAHKSCLPACVYGPAVASGYDFEREGYSLVG | 300 |
| A/Kiev/59/79_H1N1_ | AEIEDLIFLARSALILRGSVAHKSCLPACVYGPAVASGYDFEKEGYSLVG | 300 |
| A/Beijing/353/1989_H3N2_ | AEIEDLIFSARSALILRGSVAHKSCLPACVYGPAVSSGYDFEKEGYSLVG | 300 |
| A/Brazil/11/1978_H1N1_ | AEIEDLIFLARSALILRGSVAHKSCLPACVYGPAVASGYAFEKEGYSLVG | 300 |
| A/Victoria/15681/59_H2N2_ | AEIEDLIFLARSALILRGSVAHKSCLPACVYGPAVASGYDFEKEGYSLVG | 300 |
| A/NewCaledonia/20/1999_H1N1_ | AEIEDLTFLARSALILRGSVAHKSCLPACVYGPAVASGYDFEKEGYSLVG | 300 |
| A/Panama/2007/1999_H3N2_ | AEIEDLIFLARSALILRGSVAHKSCLPACVYGPAVSSGYDFEKEGYSLVG | 300 |
| r-Human Flu NP | AEFEDLTFLARSALILRGSVAHKSCLPACVYGPAVASGYDFEREGYSLVG | 300 |

Figure 10

| | | |
|---|---|---|
| A/Duck/Australia/341/83_H15N8_ | IDPFRLLQNSQIFSLIRPNENPAHKSQLVWMACHSAAFEDLRVSSFIRGI | 350 |
| A/Mallard/Astrakan/263/82_H14N8_ | IDPFRLLQNSQVFSLIRPNENPAHKSQLVWMACHSAAFEDLRVSSFIRGT | 350 |
| A/gull/Maryland/704/1977_H13N6_ | IDPFRLLQNSQVFSLIRPNENPAHKSQLVWMACHSAAFEDLRVSSFIRGT | 350 |
| A/pintail/Alberta/49/2003_H12N5_ | IDPFRLLQNSQVFSLIRPNENPAHKSQLVWMACHSAAFEDLRVSSFIRGT | 350 |
| A/duck/England/1956_H11N6_ | IDPFRLLQNSQVFSLIRPNENPAHKSQLVWMACHSAAFEDLRVLSFIRGT | 350 |
| A/pintailduck/ALB/584/1984_H10N6_ | IDPFRLLQNSQVFSLIRPNENPAHKSQLVWMACHSAAFEDLRVSSFIRGT | 350 |
| A/shorebird/DE/261/2003_H9N5_ | IDPFRLLQNSQVFSLIRPNENPAHKSQLVWMACHSAAFEDLRVSSFIRGT | 350 |
| A/turkey/Ontario/6118/1968_H8N4_ | IDPFRLLQNSQVFSLIRPNENPAHKSQLVWMACHSAAFEDLRVSSFIRGT | 350 |
| A/chicken/Germany/R28/03_H7N7_ | IDPFRLLQNSQVFSLIRPNENPAHKSQLVWMACHSAAFEDLRVSSFIRGT | 350 |
| A/shearwater/Australia/1972_H6N5_ | IDPFRLLQNSQVFSLIRPNENPAHKSQLVWMACHSAAFEDLRVSNFIRGT | 350 |
| A/blackduck/NewYork/184/1988_H5N2_ | IDPFRLLQNSQVFSLIRPNENPAHKSQLVWMACHSAAFEDLRVSSFIRGT | 350 |
| A/turkey/Ontario/7732/1966_H5N9_ | IDPFRLLQNSQVFSLIRSNENPAHKSQLVWMACHSAAFEDLRVSSFIRGT | 350 |
| r-Avian Flu NP | IDPFRLLQNSQVFSLIRSNENPAHKSQLVWMACHSAAFEDLRVSSFIRGT | 350 |
| A/HongKong/117/1977_H1N1_ | IDPFKLLQTSQVYSLIRPNENPAHKSQLVWMACNFAAFEDLRVSSFIRGT | 350 |
| A/Japan/170/62_H2N2_ | IDPFKLLQNSQVYSLIRPNENPAHKSQLVWMACNSAAFEDLRVLSFIRGT | 350 |
| A/Kitakyushu/159/93_H3N2_ | IDPFKLLQNSQVYSLIRPNENPAHKSQLVWMACHSAAFEDLRLLSFIRGT | 350 |
| A/Kumamoto/1/65_H2N2_ | IDPFKLLQNSQVYSLIRPNENPAHKSQLVWMACNSAAFEDLRVLSFIRGT | 350 |
| A/NewYork/5/2004_H3N2_ | IDPFKLLQNSQVYSLIRPNENPAHKSQLVWMACHSAAFEDLRLLSFIRGT | 350 |
| A/PuertoRico/8/34_H1N1_ | IDPFRLLQNSQVYSLIRPNENPAHKSQLVWMACHSAAFEDLRVLSFIKGT | 350 |
| A/Kiev/59/79_H1N1_ | IDPFKLLQNSQVYSLIRPNENPAHKSQLVWMACHSAAFEDLRLLSFIRGT | 350 |
| A/Beijing/353/1989_H3N2_ | IDPFKLLQNSQVYSLIRPNENPAHKSQLVWMACHSAAFEDLRLLSFIRGT | 350 |
| A/Brazil/11/1978_H1N1_ | IDPFKLLQTSQVYSLIRPNENPAHKSQLVWMACNSAAFEDLRVSSFIRGT | 350 |
| A/Victoria/15681/59_H2N2_ | IDPFKLLQNSQVYSLIRPNENPAHKSQLVWMACNSAAFEDLRVSSFIRGT | 350 |
| A/NewCaledonia/20/1999_H1N1_ | VDPFKLLQTSQVYSLIRPNENPAHKSQLVWMACNSAAFEDLRVSSFIRGT | 350 |
| A/Panama/2007/1999_H3N2_ | IDPFKLLQNSQVYSLIRPNENPAHKSQLVWMACHSAAFEDLRLLSFIRGT | 350 |
| r-Human Flu NP | IDPFRLLQNSQVYSLIRPNENPAHKSQLVWMACHSAAFEDLRVLSFIKGT | 350 |

Figure 11

| | | |
|---|---|---|
| A/Duck/Australia/341/83_H15N8_ | KVVPRGQLSTRGVQIASNENMDTMDSSTLELRSRYWAIRTRSGGNTNQQR | 400 |
| A/Mallard/Astrakan/263/82_H14N8_ | RVVPRGQLSTRGVQIASNENMETMDSSTLELRSRYWAIRTRSGGNTNQQR | 400 |
| A/gull/Maryland/704/1977_H13N6_ | RVLPRGQLSTRGVQIASNENMETMNSSTLELRSKYWAIRTRSGGNTNQQR | 400 |
| A/pintail/Alberta/49/2003_H12N5_ | RVVPRGQLSTRGVQIASNENMETMDSSTLELRSRYWAIRTRSGGNTNQQR | 400 |
| A/duck/England/1956_H11N6_ | RVVPRGQLSTRGVQIASNENMETMDSSTLELRSRYWAIRTRSGGNTNQQR | 400 |
| A/pintailduck/ALB/584/1984_H10N6_ | RVVPRGQLSTRGVQIASNENMETMDSSTLELRSRYWAIRTRSGGNTNQQR | 400 |
| A/shorebird/DE/261/2003_H9N5_ | KVIPRGQLSTRGVQIASNENMETMDSSTLELRSRYWAIRTRSGGNTSQQR | 400 |
| A/turkey/Ontario/6118/1968_H8N4_ | RVVPRGQLSTRGVQIASNENMETMDSSTLELRSRYWAIRTRSGGNTNQQR | 400 |
| A/chicken/Germany/R28/03_H7N7_ | RVVPRGQLSTRGVQIASNENMETMDSSTLELRSRYWAIRTRSGGNTNQQR | 400 |
| A/shearwater/Australia/1972_H6N5_ | RVVPRGKLSTRGVQIASNENMETMDSSTLELRSRYWAIRTRSGGNTNQQR | 400 |
| A/blackduck/NewYork/184/1988_H5N2_ | RVVPRGQLSTRGVQIASNENMETMDSSTLELRSRYWAIRTRSGGNTNQQR | 400 |
| A/turkey/Ontario/7732/1966_H5N9_ | RVVPRGQLSTRGVQIASNENMETMDSSTLELRSRYWAIRTRSGGNTNQQR | 400 |
| r-Avian Flu NP | RVVPRGQLSTRGVQIASNENMETMDSSTLELRSRYWAIRTRSGGNTNQQR | 400 |
| A/HongKong/117/1977_H1N1_ | KVIPRGKLSTRGVQIASNENMDTMGSSTLELRSRYWAIRTRSGGNTNQQR | 400 |
| A/Japan/170/62_H2N2_ | KVSPRGKLSTRGVQIASNENMDTMESSTLELRSRYWAIRTRSGGNTNQQR | 400 |
| A/Kitakyushu/159/93_H3N2_ | KVSPRGKLSTRGVQIASNENMDNMESSTLELRSRYWAIRTRSGGNTNQQR | 400 |
| A/Kumamoto/1/65_H2N2_ | KVSPRGKLSTRGVQIASNENMDTMESSTLELRSRYWAIRTRSGGNTNQQR | 400 |
| A/NewYork/5/2004_H3N2_ | KVSPRGKLSTRGVQIASNENMDNMGSSTLELRSGYWAIRTRSGGNTNQQR | 400 |
| A/PuertoRico/8/34_H1N1_ | KVLPRGKLSTRGVQIASNENMETMESSTLELRSRYWAIRTRSGGNTNQQR | 400 |
| A/Kiev/59/79_H1N1_ | KVSPRGKLSTRGVQIASNENMDTMESSTLELRSRYWAIRTRSGGNTNQQR | 400 |
| A/Beijing/353/1989_H3N2_ | KVSPRGKLSTRGVQIASNENMDNMESSTLELRSRYWAIRTRSGGNTNQQR | 400 |
| A/Brazil/11/1978_H1N1_ | KVIPRGKLSTRGVQIASNENMDTMGSSTLELRSRYWAIRTRSGGNTNQQR | 400 |
| A/Victoria/15681/59_H2N2_ | KVIPRGKLSTRGVQIASNENMDTMESSTLELRSRYWAIRTRSGGNTNQQR | 400 |
| A/NewCaledonia/20/1999_H1N1_ | RVLPRGKLSTRGVQIASNENMDAIVSSTLELRSRYWAIRTRSGGNTNQQR | 400 |
| A/Panama/2007/1999_H3N2_ | KVSPRGKLSTRGVQIASNENMDNMGSSTLELRSGYWAIRTRSGGNTNQQR | 400 |
| r-Human Flu NP | KVVPRGKLSTRGVQIASNENMETMESSTLELRSKYWAIRTRSGGNTNQQR | 400 |

Figure 12

| | | |
|---|---|---|
| A/Duck/Australia/341/83_H15N8_ | ASAGQISVQPTFSVQRNLPFERATIMAAFTGNTEGRTSDMRTEIIRMMES | 450 |
| A/Mallard/Astrakan/263/82_H14N8_ | ASAGQISVQPTFSVQRNLPFERATIMAAFTGNTEGRTSDMRTEIIRMMES | 450 |
| A/gull/Maryland/704/1977_H13N6_ | ASAGQVSVQPTFSVQRNLPFERATIMAAFTGNTEGRTSDMRTEIIRMMEN | 450 |
| A/pintail/Alberta/49/2003_H12N5_ | ASAGQISVQPTFSVQRNLPFERATIMAAFTGNTEGRTSDMRTEIIRMMEN | 450 |
| A/duck/England/1956_H11N6_ | ASAGQISVQPTFSVQRNLPFERATIMAAFTGNTEGRTSDMRTEIIRMMES | 450 |
| A/pintailduck/ALB/584/1984_H10N6_ | ASAGQISVQPTFSVQRNLPFERATIMAAFTGNTEGRTSDMRTEIIRMMEN | 450 |
| A/shorebird/DE/261/2003_H9N5_ | ASAGQISVQPTFSVQRNLPFERATIMAAFTGNTEGRTSDMRTEIIRMMEN | 450 |
| A/turkey/Ontario/6118/1968_H8N4_ | ASAGQISVQPTFSVQRNLPFERATIMAAFTGNTEGRTSDMRTEIIRMMEN | 450 |
| A/chicken/Germany/R28/03_H7N7_ | ASAGQISVQPTFSVQRNLPFERATIMAAFTGNTEGRTSDMRTEIIRMMES | 450 |
| A/shearwater/Australia/1972_H6N5_ | ASAGQISVQPTFSVQRNLPFERATIMAAFTGNTEGRTSDMRTEIIRMMES | 450 |
| A/blackduck/NewYork/184/1988_H5N2_ | ASAGQISVQPTFSVQRNLPFERATIMAAFTGNTEGRTSDMRTEIIRMMEN | 450 |
| A/turkey/Ontario/7732/1966_H5N9_ | ASAGQISVQPTFSVQRNLPFERATIMAAFTGNTEGRTSDMRTEIIKMMEN | 450 |
| r-Avian Flu NP | ASAGQISVQPTFSVQRNLPFERATIMAAFTGNTEGRTSDMRTEIIKMMEN | 450 |
| A/HongKong/117/1977_H1N1_ | ASAGQISIQPTFSVQRNLPFDKTTIMAAFTGNAEGRTSDMRAEIIKMMES | 450 |
| A/Japan/170/62_H2N2_ | ASAGQISVQPAFSVQRNLPFDKPTIMAAFTGNTEGRTSDMRAEIIRMMEG | 450 |
| A/Kitakyushu/159/93_H3N2_ | ASAGQISVQPTFSVQRNLPFEKSTVMAAFTGNTEGRTSDMRAEIIRMMEG | 450 |
| A/Kumamoto/1/65_H2N2_ | ASAGQISVQPAFSVQRNLPFDKPTIMAAFTGNTEGRTSDMRAEIIRMMEG | 450 |
| A/NewYork/5/2004_H3N2_ | ASAGQISVQPTFSVQRNLPFEKSTVMAAFTGNTEGRTSDMRAEIIRMMEG | 450 |
| A/PuertoRico/8/34_H1N1_ | ASAGQISIQPTFSVQRNLPFDRTTIMAAFNGNTEGRTSDMRTEIIRMMES | 450 |
| A/Kiev/59/79_H1N1_ | ASAGQISVQPTFSVQRNLPFDKSTVMAAFTGNTEGRTSDMRAEIIRMMED | 450 |
| A/Beijing/353/1989_H3N2_ | ASAGQISVQPTFSVQRNLPFEKSTVMAAFTGNTEGRTSDMRAEIIRMMEG | 450 |
| A/Brazil/11/1978_H1N1_ | ASAGQISIQPTFSVQRNLPFDKTTIMAAFTGNAEGRTSDMRAEIIRMMES | 450 |
| A/Victoria/15681/59_H2N2_ | ASAGQISVQPTFSVQRNLPFDKPTIMAAFTGNAEGRTSDMRAEIIRMMEG | 450 |
| A/NewCaledonia/20/1999_H1N1_ | ASAGQISTQPTFSVQRNLPFDKTTIMAAFTGNTEGRTSDMRAEIIKMMES | 450 |
| A/Panama/2007/1999_H3N2_ | ASAGQISVQPTFSVQRNLPFEKSTVMAAFTGNTEGRTSDMRAEIIRMMEG | 450 |
| r-Human Flu NP | ASAGQISIQPTFSVQRNLPFDRTTIMAAFTGNTEGRTSDMRTEIIRMMES | 450 |

Figure 13

| | | |
|---|---|---|
| A/Duck/Australia/341/83_H15N8_ | AKPEDVSFQGRGVFELSDEKATNPIVPSFDMNNEGSYFFGDNAEEYDN------ | 498 |
| A/Mallard/Astrakan/263/82_H14N8_ | ARPEDVSFQGRGVFELSDEKATNPIVPSFDMSNEGSYFFGDNAEEYDN------ | 498 |
| A/gull/Maryland/704/1977_H13N6_ | SRPEDVSFQGRGVFELSDEKATNPIVPSFDMSNEGSYFFGDNAEEFDS------ | 498 |
| A/pintail/Alberta/49/2003_H12N5_ | ARPEDVSFQGRGVFELSDEKATNPIVPSFDMSNEGSYFFGDNAEEYDN------ | 498 |
| A/duck/England/1956_H11N6_ | ARPEDVSFQGRGVFELSDEKATNPIVPSFDMSKEGSYFFGDNAEEYDN------ | 498 |
| A/pintailduck/ALB/584/1984_H10N6_ | ARPEDVSFQGRGVFELSDEKATNPIVPSFDMSNEGSYFFGDNAEEYDN------ | 498 |
| A/shorebird/DE/261/2003_H9N5_ | ARPEDVSFQGRGVFELSDEKATNPIVPSFDMSNEGSYFFGDNAEEYDN------ | 498 |
| A/turkey/Ontario/6118/1968_H8N4_ | ARPEDVSFQGRGVFELSDEKATNPIVPSFDMSNEGSYFFGDNAEEYDN------ | 498 |
| A/chicken/Germany/R28/03_H7N7_ | ARPEDVSFQGRGVFELSDEKATNPIVPSFDMSNEGSYFFGDNAEEYDN------ | 498 |
| A/shearwater/Australia/1972_H6N5_ | ARPEDVSFQGRGVFELSDEKATNPIVPSFDMSNEGSYFFGDNAEEYDN------ | 498 |
| A/blackduck/NewYork/184/1988_H5N2_ | ARPEDVSFQGRGVFELSDEKATNPIVPSFDMSNEGSYFFGDNAEEYDN------ | 498 |
| A/turkey/Ontario/7732/1966_H5N9_ | ARPEDVSFQGRGVFELSDEKATNPIVPSFDMSNEGSYFFGDNAEEYDN------ | 498 |
| r-Avian Flu NP | ARPEDVSFQGRGVFELSDEKATNPIVPSFDMSNEGSYFFGDNAEEYDNHHHHHH | 504 |
| A/HongKong/117/1977_H1N1_ | ARPEEVSFQGRGVFELSDERAANPIVPSFDMSNEGSYFFGDNAEEYDN------ | 498 |
| A/Japan/170/62_H2N2_ | AKPEEMSFQGRGVFELSDEKATNPIVPSFDMSNEGSYFFGDNAEEYDN------ | 498 |
| A/Kitakyushu/159/93_H3N2_ | AKPEEVSFRGRGVFELSDEKATNPIVPSFDMSNEGSYFFGDNAEEYDN------ | 498 |
| A/Kumamoto/1/65_H2N2_ | AKPEEMSFQGRGVFELSDEKATNPIVPSFDMSNEGSYFFGDNAEEYDN------ | 498 |
| A/NewYork/5/2004_H3N2_ | AKPEEVSFRGRGVFELSDEKATNPIVPSFEMSNEGSYFFGDNAEEYD------- | 497 |
| A/PuertoRico/8/34_H1N1_ | ARPEDVSFQGRGVFELSDEKAASPIVPSFDMSNEGSYFFGDNAEEYDN------ | 498 |
| A/Kiev/59/79_H1N1_ | AKPEEVSFRGRGVFELSDEKATNPIVPSFDMSNEGSYFFGDNAEEYDN------ | 498 |
| A/Beijing/353/1989_H3N2_ | AKPEEVSFRGRGVFELSDEKATNPIVPSFDMSNEGSYFFGDNAEEYDN------ | 498 |
| A/Brazil/11/1978_H1N1_ | ARPEEVSFQGRGVFELSDERAANPIVPSFDMSNEGSYFFGDNAEEYDN------ | 498 |
| A/Victoria/15681/59_H2N2_ | AKPEEVSFQGRGVFELSDEKATNPIVPSFDMSNEGSYFFGDNAEEYDN------ | 498 |
| A/NewCaledonia/20/1999_H1N1_ | ARPEEVSFQGRGVFELSDERATNPIVPSFDMSNEGSYFFGDNAEEYDN------ | 498 |
| A/Panama/2007/1999_H3N2_ | AKPEEVSFRGRGVFELSDEKATNPIVPSFEMSNEGSYFFGDNAEEYDN------ | 498 |
| r-Human Flu NP | ARPEDVSFQGRGVFELSDEKAASPIVPSFDMSNEGSYFFGDNAEEYDNHHHHHH | 504 |

RAPID DIAGNOSIS METHOD SPECIFIC TO AVIAN INFLUENZA VIRUS

TECHNICAL FIELD

The present invention relates to a method for detecting an avian influenza virus and an immunochromatographic test tool for detecting an avian influenza virus.

BACKGROUND ART

Influenza viruses are classified into type-A, type-B and type-C, based on differences between an antigenicity of a nucleoprotein(NP) and that of a membrane protein (M). Regarding an influenza type-A virus in the influenza viruses, there are the same number of subtypes as the number of combinations of hemagglutinins (HAs) and neuraminidases (NAs), based on differences in amino acid sequences of HAs and NAs or differences in their antigenicities, in which the HAs are classified into 15 kinds including H1 to H15 and the NAs are classified into 9 kinds including N1 to N9. Among them, the subtypes each causing an infection in human as a host are subtypes H1 to H3 and N1 to N2. In addition, each of an influenza type-A virus (H1 to H3, or N1 to N2) and an influenza type-B virus (hereinafter also referred to as "human influenza virus") is a causative virus for so-called "influenza (human influenza)" causing a pandemic year after year.

The influenza type-A virus infects not only human but also many mammals and avian species. An infectious disease in avian species caused by the infection in avian species with the influenza type-A virus is "avian influenza". As an avian influenza virus, which is a causative virus of the avian influenza, all of subtypes H1 to H15 and subtypes N1 to N9 are confirmed. Most of avian influenza viruses do not cause serious symptoms. However, among viruses belonging to avian influenza virus subtypes H5 and H7, there is a virus causing serious symptom in the case where avian species are infected therewith. These are so-called "high-pathogenic avian influenza viruses", which are apprehensive about a human infection. Since there are some cases of infections and disease contractions in human who has contacted with an animal infected with H9 subtype in the avian influenza viruses, the spread of a human infection is feared.

Presently, in clinical practice, a diagnosis of influenza has been carried out by using a kit for rapidly detecting an influenza virus antigen. Such a rapid diagnosis kit includes a kit employing an enzyme immunoassay (EIA) or an immunochromatography as a principle. There are included a kit for detecting the influenza type-A virus only (see, for example, Japanese Patent Publication Number: JP 2006-67979), a kit for collectively detecting both of the influenza type-A virus and the influenza type-B virus, a kit for separately detecting the influenza type-A virus and the influenza type-B virus, and the like.

However, the rapid diagnosis kit of the patent document 1 is a kit for detecting a wide spectrum of viruses each belonging to the influenza type-A virus, without distinguishing between the human influenza type-A virus and the avian influenza virus. Accordingly, in the case where human shows signs of influenza, it is impossible to determine whether the signs are caused by the avian influenza virus or the human influenza virus. Therefore, it has been required to develop a method for rapidly diagnosing the avian influenza virus.

DISCLOSURE OF INVENTION

The present invention has been made in view of such a circumstance. The object of the present invention is to provide a method for detecting an avian influenza virus specifically, rapidly and in a simple manner, as distinguishing the avian influenza virus from a human influenza virus, and an immunochromatographic test tool for use in the method.

In the present invention, in order to achieve the above-mentioned purposes, the following technical measures have been taken.

The present invention regarding the method for detecting the avian influenza virus is characterized by detecting an avian influenza virus in a sample by an immunological assay, with the use of an anti-influenza virus antibody being unreactive to human influenza type-A virus subtypes H1, H2 and H3 and a human influenza type-B virus and being reactive to plural subtypes of avian influenza viruses.

In the method for detecting the avian influenza virus, it is preferred that at least one of the avian influenza virus subtypes to which the anti-influenza virus antibody is reactive be selected from the group consisting of avian influenza virus subtypes H5, H7 and H9.

In the method for detecting the avian influenza virus, the anti-influenza virus antibody may be an antibody being reactive to at least subtypes H3 to H15 of avian influenza virus.

In the method for detecting the avian influenza virus, as the above-mentioned anti-influenza virus antibody, there can be used an antibody against a nucleoprotein of an influenza type-A virus. Also, there can be used an antibody recognizing an epitope localized in a region at positions 46 to 159 from the N-terminal side of an amino acid sequence of a nucleoprotein of the avian influenza virus.

In addition, in the above method for detecting the avian influenza virus, it is preferred that the anti-influenza virus antibody be a monoclonal antibody produced by the hybridoma of which acceptance number of international deposit is FERM ABP-10904 (the accession number of the domestic deposit: FERM P-20822).

Further, in the above-mentioned method for detecting the avian influenza virus, it is preferred that the immunological assay include the step of using a primary antibody against an influenza virus and a secondary antibody against the influenza virus, to form a complex containing a labeled antibody of the primary antibody, the secondary antibody immobilized on a solid phase and the influenza virus, wherein at least the secondary antibody is an anti-influenza virus antibody being unreactive to human influenza type-A virus subtypes H1, H2 and H3 and a human influenza type-B virus and being reactive to plural subtypes of avian influenza viruses.

It is preferred that each of the primary antibody and the secondary antibody be an anti-influenza virus antibody being unreactive to human influenza type-A virus subtypes H1, H2 and H3 and a human influenza type-B virus and being reactive to plural subtypes of avian influenza viruses.

It is preferred that the above-mentioned immunological assay be an immunochromatography.

It is preferred that the above-mentioned immunochromatography comprise the step of forming the complex containing the secondary antibody, the labeled antibody of the primary antibody and the influenza virus on the immunochromatographic membrane carrier having the secondary antibody immobilized thereon, wherein the above-mentioned secondary antibody is an anti-influenza virus antibody being unreactive to human influenza type-A virus subtypes H1, H2 and H3 and a human influenza type-B virus and being reactive to plural subtypes of avian influenza viruses.

The present invention regarding an immunochromatographic test tool is an immunochromatographic test tool for detecting an avian influenza virus in a sample by utilizing a primary antibody against an influenza virus and a second antibody against an influenza virus, comprising a sample addition member to which the sample is applied;

a label holding member in which a primary antibody labeled with a labeling substance is hold; and an immunochromatographic membrane carrier having a judgment region placed thereon, wherein the judgment region is a region having the secondary antibody immobilized thereon;

wherein the primary antibody is an anti-influenza virus antibody being reactive to an avian influenza virus, and wherein the secondary antibody is an anti-influenza virus antibody being unreactive to human influenza type-A virus subtypes H1, H2 and H3 and a human influenza type-B virus and being reactive to plural subtypes of avian influenza viruses.

In the above-mentioned immunochromatographic test tool, it is preferred that the above-mentioned labeling substance be an insoluble granular maker. In addition, among them, a colored synthetic polymer particle or a colloidal metallic particle is particularly preferred.

BRIEF DESCRIPTION OF DRAWINGS

FIG. 4 is a diagram showing amino acid sequences at positions 1 to 50 of each of r-Human Flu NP(SEQ ID NO:9), r-Avian Flu NP(SEQ ID NO:10), A/Duck/Australia/341/83 H15N8 (SEQ ID NO: 15), A/Mallard/Astrakan/263/82 H14N8 (SEQ ID NO: 16), A/gull/Maryland/704/1977 H13N6 (SEQ ID NO: 17), A/pintail/Alberta/49/2003 H12N5 (SEQ ID NO: 18), A/duck/England/1956 H11N6 (SEQ ID NO: 19), A/pintailduck/ALB/584/1984 H10N6 (SEQ ID NO: 20), A/shorebird/DE/261/2003 H9N5 (SEQ ID NO: 21), A/turkey/Ontario/6118/1968 H8N4 (SEQ ID NO: 22), A/chicken/Germany/R28/03 H7N7 (SEQ ID NO: 23), A/shearwater/Australia/1972 H6N5 (SEQ ID NO: 24), A/blackduck/NewYork/184/1988 H5N2 (SEQ ID NO: 25), A/turkey/Ontario/7732/1966 H5N9 (SEQ ID NO: 26), A/HongKong/117/1977 H1N1 (SEQ ID NO: 27), A/Japan/170/62 H2N2 (SEQ ID NO: 28), A/Kitakyushu/159/93 H3N2 (SEQ ID NO: 29), A/Kumamoto/1/65 H2N2 (SEQ ID NO: 30), A/NewYork/5/2004 H3N2 (SEQ ID NO: 31), A/PuertoRico/8/34 H1N1 (SEQ ID NO: 32), A/Kiev/59/79 H1N1 (SEQ ID NO: 33), A/Beijing/353/1989 H3N2 (SEQ ID NO: 34), A/Brazil/11/1978 H1N1 (SEQ ID NO: 35), A/Victoria/15681/59 H2N2 (SEQ ID NO: 36), A/NewCaledonia/20/1999 H1N1 (SEQ ID NO: 37), and A/Panama/2007/1999 H3N2 (SEQ ID NO: 38);

FIG. 5 is also a diagram showing amino acid sequences at positions 51 to 100 of each of SEQ ID Nos. 9 and 10 , and SEQ ID Nos: 15-38;

FIG. 6 is also a diagram showing amino acid sequences at positions 101 to 150 of each of SEQ ID Nos. 9 and 10, and SEQ ID Nos: 15-38;

FIG. 7 is also a diagram showing amino acid sequences at positions 151 to 200 of each of SEQ ID Nos. 9 and 10, and SEQ ID Nos: 15-38;

FIG. 8 is also a diagram showing amino acid sequences at positions 201 to 250 of each of SEQ ID Nos. 9 and 10, and SEQ ID Nos: 15-38;

FIG. 9 is also a diagram showing amino acid sequences at positions 251 to 300 of each of SEQ ID Nos. 9 and 10, and SEQ ID Nos: 15-38;

FIG. 10 is also a diagram showing amino acid sequences at positions 301 to 350 of each of SEQ ID Nos. 9 and 10, and SEQ ID Nos: 15-38;

FIG. 11 is also a diagram showing amino acid sequences at positions 351 to 300 of each of SEQ ID Nos. 9 and 10, and SEQ ID Nos: 15-38;

FIG. 12 is also a diagram showing amino acid sequences at positions 401 to 450 of each of SEQ ID Nos. 9 and 10, and SEQ ID Nos: 15-38;

FIG. 13 is also a diagram showing amino acid sequences at positions 451 to 400 of each of SEQ ID Nos. 9 and 10, and SEQ ID Nos: 15-38;

BEST MODE FOR CARRYING OUT THE INVENTION

Figure 1:
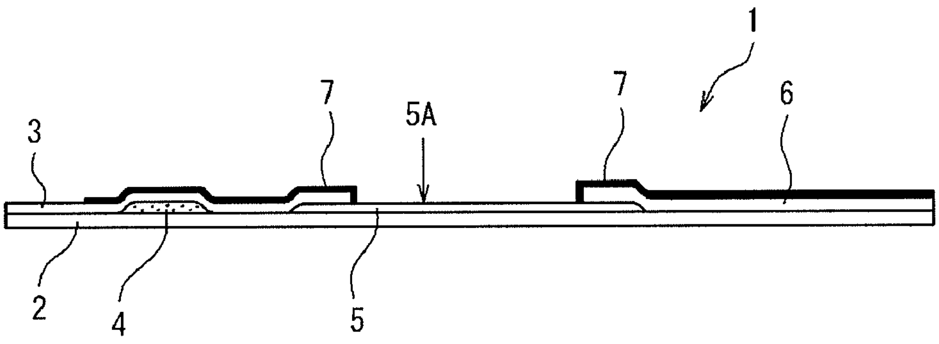
FIG. 1 is a cross-sectional view of an immunochromatographic test tool according to one embodiment of the present invention.

The method for detecting an avian influenza virus is a method having the step of detecting an avian influenza virus in a sample by an immunological assay, with the use of an anti-influenza virus antibody being unreactive to human influenza type-A virus subtypes H1, H2 and H3 and a human influenza type-B virus and being reactive to plural subtypes of avian influenza viruses.

According to the present detection method, plural subtypes of avian influenza viruses can be detected as distinguishing the avian influenza virus from the human influenza virus, since the above-mentioned antibody is used in the present detection method, while according to the previous method, the virus could be only detected as the influenza type-A virus without distinguishing the avian influenza virus from the human influenza type-A virus.

The antibody used in the method for detecting the avian influenza virus is an anti-influenza virus antibody being unreactive to human influenza type-A virus subtypes H1, H2 and H3 and a human influenza type-B virus and being reactive to plural subtypes of avian influenza viruses. Since this anti-influenza virus antibody is unreactive to human influenza viruses (type-A (subtypes H1 to H3) and type-B) and being reactive to plural subtypes of avian influenza viruses, an avian influenza type-A virus can be detected as distinguishing an avian origin from a human origin, while conventionally, the influenza type-A virus had been detected without distinguishing an avian origin from a human origin.

It is preferred that at least one of avian influenza virus subtypes to which the anti-influenza virus antibody is reactive be selected from the group consisting of avian influenza virus subtypes H5, H7 and H9. The reasons therefor are that since the avian influenza virus subtype H5, H7 or H9 is the avian influenza of which infection in human has been confirmed, there is a possibility that these subtypes cause a spreaded infection among human.

The anti-influenza virus antibody may be an antibody being reactive to at least subtypes H3 to H15 of avian influenza viruses. In this case, the avian influenza virus can be detected, as long as the avian influenza virus is any one of subtypes H3 to H15.

It is preferred that the anti-influenza virus antibody be an antibody against a nucleoprotein of the influenza type-A virus. It is also preferable to use, as the anti-influenza virus antibody, an antibody recognizing an epitope localized in a region of positions at 46 to 159 from the N-terminal side of an amino acid sequence of a nucleoprotein of an avian influenza virus.

Concrete Examples of the anti-influenza virus antibody include a monoclonal antibody (hereinafter referred to as “4E3”) produced by the hybridoma Mouse-Mouse hybridoma 4E3.

The hybridoma has been named and designated as Mouse-Mouse hybridoma 4E3 and has been deposited under the accession number FERM BP-10904 (acceptance number FERM ABP-10904 [the date received: Aug. 30, 2007; the accession number of the domestic deposit: FERM P-20822; the date of the domestic deposit: Feb. 24, 2006]), under the Budapest Treaty with International Patent Organism Depositary of the National Institute of Advanced Industrial Science and Technology, of which address is Central 6, 1-1, Higashi 1-chome, Tsukuba-shi, Ibaraki 305-8566, Japan.

This hybridoma is a fusion cell of a mouse myeloma cell strain and a mouse lymphocyte. In addition, the hybridoma produces a monoclonal antibody (4E3) binding to a nucleoprotein (NP) of each of influenza type-A virus subtypes H3 to H15. The 4E3 can be produced by, for example, culturing the hybridoma Mouse-Mouse hybridoma 4E3 in RPMI 1640 medium(SIGMA R6504) containing 10% fetal bovine serum, 10 mM L-glutamine and 0.25% $NaHCO_3$ at 37° C. in 5% $CO_2$; and recovering and purifying the produced 4E3 by the known methods.

This monoclonal antibody encompasses a fragment thereof, a modified antibody such as a chimeric antibody thereof and a humanized antibody, and a mutant antibody. Each of the fragment, the modified antibody and the mutant antibody has the same specificity to plural subtypes of avian influenza viruses as that of the original antibody. These antibodies or fragments can be produced by the procedures or methods known by one of ordinary skill in the art.

The immunological assay (immunoassay) is a method for determining quantitatively a substance on the basis of a binding capacity of an antibody. As the immunological assay, there can be used, for example, a radioimmunoassay (RIA), an immunoradiometric assay (IRMA), an enzyme immunoassay (EIA), an enzyme-linked immunosorbent assay (ELISA), a homogeneous enzyme immunoassay, a fluorescence immunoassay (FIA), an immunofluorometric assay (IFMA), a fluorescence polarization, a chemiluminescent immunoassay (CLIA), a chemiluminescent enzyme immunoassay (CLEIA), or an immunochromatography. As the above-mentioned anti-influenza virus antibody in immunological assay, one or more kinds of antibodies can be used.

There can be used as the sample, a sample to be suspected to contain an influenza virus. The sample may be a mixture of a biological sample of a subject to be suspected and a solvent, wherein the biological sample includes, for example, tear, eye mucus, expectoration, saliva, stool and the like and wherein the solvent includes, for example, a saline, a phosphate buffer and the like; a sample obtained by washing or extracting with the above-mentioned solvent a gauze or swab by which an affected part of a subject to be suspected (e.g., cavitas nasi, pharynx or the like) was wiped; or washings obtained by washing with the above-mentioned solvent an affected part of a subject to be suspected.

Among these immunological assays, preferred is an immunological assay based on a sandwich technique as a principle, including the step of using a primary antibody against an influenza virus and a secondary antibody against an influenza virus, to form a complex containing a labeled antibody of the primary antibody, the secondary antibody immobilized on a solid phase and the influenza virus.

In this method, as at least the secondary antibody, there are used the above-mentioned anti-influenza virus antibody being unreactive to human influenza type-A virus subtypes H1, H2 and H3 and the human influenza type-B virus and being reactive to plural subtypes of avian influenza viruses. The reason therefor is that an avian influenza virus in a sample can be determined sensitively by constructing so-called “sandwich structure” with a primary antibody, an avian influenza virus (antigen) and a secondary antibody.

It is preferred that each of the above-mentioned primary antibody and the above-mentioned secondary antibody be the above-mentioned anti-influenza virus antibody. Using the above-mentioned anti-influenza virus antibody as both of the primary antibody and the secondary antibody, the sensitivities and specificities thereof can be increased, thereby resulting in an improvement of the detection accuracy.

The immunological assay utilizing a sandwich technique as a principle of assay includes IRMA, ELISA, IFMA, immunochromatography and the like.

A labeling substance which is to be bound to a primary antibody includes a radioisotope ($^{125}I$, $^{14}C$, $^{32}P$ or the like), an enzyme (β-galactosidase, peroxidase, alkaline phosphatase or the like), a fluorescent substance (a fluorescein derivative, a rhodamine derivative or the like), an insoluble granular marker and the like.

The raw materials or shapes of the solid phase having the secondary antibody immobilized thereon can be appropriately selected depending on assays. The raw materials for the solid phase include, for example, synthetic organic macromolecular compounds such as polyvinyl chloride, polyvinylidene fluoride(PVDF), polystyrene, styrene-divinylbenzene copolymer, styrene maleic anhydride copolymer, nylon, polyvinyl alcohol, polyacrylamide, polyacrylonitrile and polypropylene; polysaccharides such as dextran derivative, agarose gel and cellulose; and inorganic macromolecular compounds such as a glass, a silica gel and a silicone. These compounds can be a compound to which a functional group such as an amino group, an aminoacyl group, a carboxyl group, an acyl group, a hydroxyl group and a nitro group had been introduced. Shape of the solid phase can be, for example, tabular shape like that of a microtiter plate (ELISA plate) or a disc; granulous shape like that of beads; tubular shape like that of a test tube or a tube; fibriform; or membranal shape.

Among the immunological assays employing a sandwich method as a principle thereof, the immunochromatography is preferred. The reasons therefor are that a determination can be carried out rapidly, in an easy operation without using any special devices.

It is preferred that the above-mentioned immunochromatography include the step of forming the complex containing the secondary antibody, the labeled antibody of the primary antibody and the influenza virus on the immunochromatographic membrane carrier having the secondary antibody immobilized thereon, wherein the secondary antibody is an anti-influenza virus antibody being unreactive to human influenza type-A virus subtypes H1, H2 and H3 and the human influenza type-B virus and being reactive to plural subtypes of avian influenza viruses. In this case, since the complex of the primary antibody, the antigen and the secondary antibody (sandwich structure) is formed on the immunochromatographic membrane carrier, an avian influenza virus can be detected by recognizing a labeling for the primary antibody.

Also in the immunochromatography, the above-mentioned labeling substances can be used. Among them, an insoluble granular marker can be preferably used, since a rapid and simple determination can be achieved by observing a color with the naked eyes. The insoluble granular marker refers to a particle capable of coloring by itself among particles used as the labeling substance in the immunochromatography. Examples are a colloidal metal particle such as gold colloid and a platinum colloid; a synthetic polymer particle such as a polystyrene colored by a pigment or the like (colored synthetic polymer particle); a polymerized-dye particle and the like.

FIG. 1 is a cross-sectional view of the immunochromatographic test tool of one embodiment of the present invention. A immunochromatographic test tool 1 comprises a substrate 2 made of a plastic plate having an adhesive layer on the surface thereof on which a sample addition member 3 made of a rayon non-woven fabric, a label holding member 4 made of a glass fiber non-woven fabric, a immunochromatographic membrane carrier 5 made of a nitrocellulose porous body, and an absorption member 6 made of a cellulose non-woven fabric are provided.

The substrate 2 is used for arranging appropriately the above-mentioned members including the sample addition member 3, the label holding member 4 and the like thereon. The substrate 2 can be prepared from a variety of materials such as a paper, and a glass in addition to the plastic.

To the sample addition member 3, a sample is applied. As the sample, the same sample as used in the above-mentioned immunological assay can be used. Preferred are a rhinal aspirate fluid, a rhinal swab, and a pharyngeal swab. The sample may be diluted with an appropriate solvent such as a buffer, and added to the sample addition member 3. For preparing the sample addition member 3 used are, for example, a sheet or a film made of a porous synthetic resin such as a porous polyethylene and a porous polypropylene; a cellulose paper, a fabric cloth or a nonwoven fabric cloth, such as a paper filter and a cotton cloth; a nonwoven fabric cloth made of a glass, in addition to the rayon nonwoven fabric cloth.

The label holding member 4 is arranged in contact with the sample addition member 3 and supports the primary antibody labeled with a labeling substance therein. This primary antibody reacts with an analyte in a sample in an antigen-antibody reaction. As the primary antibody, used is an antibody being reactive to an avian influenza virus. As long as the antibody is reactive to an avian influenza virus, one or more kinds of antibodies can be used. Preferably, 4E3 is used as the primary antibody. Further, a combination of 4E3 and an anti-influenza virus antibody being reactive to other avian influenza can be used.

As a labeling substance for labeling the primary antibody, there can be used the same labeling substances used in the immunochromatography employing the above-mentioned sandwich method as a principle. Among them, preferred is an insoluble granular maker, and particularly preferred is a colored synthetic polymer particle or a colloidal metal particle, since a rapid and simple determination can be achieved by observing changes in a color with the naked eyes.

The label holding member 4 can be prepared by, for example, impregnating a nonwoven fabric cloth made of a glass fiber with a suspension of a labeled primary antibody; and then drying the resulting cloth. Here, a nonwoven fabric cloth made of a glass fiber has been used as the label holding member 4, but usable material is not limited thereto. For preparing the label holding member 4, there can be used a cloth made of celluloses (e.g., a paper filter, a nitrocellulose membrane or the like), a cloth made of a porous plastic such as polyethylene, polypropylene or the like.

The immunochromatographic membrane carrier 5 is arranged so as to keep a gap with the label holding member 4, and has a judgment region 5A having the secondary antibody immobilized thereon, wherein the secondary antibody is an antibody causing an antigen-antibody reaction with an analyte. The secondary antibody is an anti-influenza virus antibody being unreactive to human influenza type-A virus subtypes H1, H2 and H3 and a human influenza type-B virus and being reactive plural subtypes of avian influenza viruses. Preferable secondary antibody is 4E3.

As the immunochromatographic membrane carrier 5, a nitrocellulose porous body has been used. However, any carriers can be used as the immunochromatographic membrane carrier 5, as long as the carrier is capable of developing chromatographically an analyte contained in a sample and immobilizing the secondary antibody for forming the above-mentioned judgment region 5A. There also can be used a membrane made of other celluloses (for example, cellulose acetate), a membrane made of nylon (for example, a modified nylon having an amino group introduced thereto, wherein the amino acid may have a substituent, such as a carboxyl group, or an alkyl group), a membrane made of polyvinylidene-fluoride (PVDF) or the like.

The absorption member 6 is arranged in contact with the immunochromatographic membrane carrier 5, which is used for absorbing an excess sample. The absorption member 6 may be prepared by a material capable of absorbing rapidly and holding a liquid, including cotton cloth; a paper filter; and a porous-plastic nonwoven fabric made of polyethylene, polypropylene or the like. In addition, a part of the sample addition member 3 and the surface of the absorption member 6 are covered with a transparent sheet 7, as shown in FIG. 1.

For example, the immunochromatographic test tool 1 of the present invention can be prepared as follows. First, the immunochromatographic membrane carrier 5 is attached to the midpoint of the substrate 2. The label holding member 4 is attached to the upstream of the substrate 2 so as to keep a gap in order to avoid contact with the end on the side of the starting point for chromatographic development on the immunochromatographic membrane carrier 5 (namely, left side in FIG. 1, hereinafter referred to as “upstream”). The upstream part of the sample addition member 3 is attached to the uppermost stream part of the substrate 2, while a part on the side of the end point for chromatographic development on the sample addition member 3 (namely, the right side in FIG. 1, hereinafter referred to as “downstream”) is mounted to the top surface on the upstream part of each of the label holding member 4 and the immunochromatographic membrane carrier 5, and attached to the substrate 2 located between the label holding member 4 and the immunochromatographic membrane carrier 5. In addition, the upstream part of the absorption member 6 is attached to the top surface of the downstream part of the immunochromatographic membrane carrier 5, and the downstream part of the absorption member 6 is attached to the lowermost stream part of the substrate 2. Then, the surfaces of the downstream part of the sample addition member 3 and the absorption member 6 are covered with the transparent sheet 7.

Optionally, a sample is mixed with appropriate solvent, to give a mixture capable of being developed chromatographically. Thereafter, the upstream of the above-mentioned immunochromatographic test tool 1 (sample addition member 3) is immersed in the mixture, whereby the mixture passes through the sample addition member 3 to be mixed with a labeled primary antibody on the label holding member 4.

On this occasion, in the case where an avian influenza virus (antigen) is present in the above-mentioned mixture, the label holding member 4 is bound to the primary antibody in an antigen-antibody reaction, thereby forming a complex.

This complex is developed chromatographically in the immunochromatographic membrane carrier 5, to reach the judgment region 5A. Thereafter, the complex is captured at the region by causing antigen-antibody reaction with the secondary antibody immobilized to the region.

On this occasion, in the case where colored synthetic polymer particles such as a blue latex particle were used as a labeling substance, the judgment region 5A is blued by an aggregation of the particles. Therefore, the presence of the avian influenza virus can be immediately and visually confirmed.

Therefore, using this immunochromatographic test tool 1, there can be confirmed whether or not the influenza virus causative for a cases of human infection with influenza is avian origin, since an anti-influenza virus antibody being unreactive to human influenza virus (type-A (H1 to H3 subtypes) and type-B) and being reactive to plural subtypes of avian influenza viruses is used in the tool.

The immunochromatographic membrane carrier 5 can comprise not only one judgment region but also two or more judgment regions. In addition, the immunochromatographic membrane carrier 5 may comprise a control member. In the case where the carrier 5 comprises the control member, an avidin labeled with red-colored latex particle is kept on the label holding member 4 and a biotin which binds specifically to the avidin is immobilized on the control part of the immunochromatographic membrane carrier 5. In addition, for example, a hapten such as 2,4-dinitrophenol (DNP) and an antibody recognizing the hapten can be used in a combination, instead of a combination of avidin and biotin. In this case, it is preferable to use a hapten which is not present in a sample used in the assay.

In addition, the subtype to which the anti-influenza virus antibody used in the method for detecting an avian influenza virus of the present invention is reactive is not limited to subtypes up to H15. The subtype encompasses a subtype H16 which is confirmed as a subtype of an influenza type-A virus, and subtype H17 or subsequent subtypes which will be confirmed in the future.

EXAMPLES

The present invention is hereinafter concretely described by means of the following Examples, Comparative Examples and Test Examples, without intending to limit the scope of the present invention thereto.

Each of antibodies used in immunochromatographic test tools of the Examples and the Comparative Examples is a monoclonal antibody 4E3 produced by the above-explained hybridoma [the acceptance number of the international deposit: FERM ABP-10904 (the accession number of the domestic deposit: FERM P-20822) in International Patent Organism Depositary of the National Institute of Advanced Industrial Science and Technology] and a monoclonal antibody (hereinafter referred to as "1C10") produced by hybridoma Mouse-Mouse hybridoma 1C10.

The hybridoma has been named and designated as Mouse-Mouse hybridoma 1C10 and has been deposited under the acceptance number FERM ABP-10903 [the date received: Aug. 30, 2007; the accession number of the domestic deposit: FERM P-20821; the date of the domestic deposit: Feb. 24, 2006], under the Budapest Treaty with International Patent Organism Depositary of the National Institute of Advanced Industrial Science and Technology, of which address is Central 6, 1-1, Higashi 1-chome, Tsukuba-shi, Ibaraki 305-8566, Japan.

Here, a reactivity of 4E3 or 1C10 to an influenza virus was examined by Enzyme labeled antibody method with MDCK cell infected with an influenza virus. Influenza virus and MDCK cell were incubated for 12 hours in a well of 96-well micro plate, to thereby infect the influenza virus to the MDCK cell. Next, the infected MDCK cell was fixed with ethanol, and then incubated for 30 minutes with a supernatant obtained by culturing a hybridoma which produces 4E3 or a supernatant obtained by culturing a hybridoma which produces 1C10. After the incubation, the incubated cell was washed with PBS and then reacted with a peroxidase-labeled anti-mouse immunoglobulin antibody for 30 minutes. After the reaction, the resulting mixture was washed with PBS. Thereafter, diaminobenzidine was added to the resulting mixture, to thereby visualize the anti-mouse immunoglobulin antibody. In this method, when the influenza virus infected to MDCK cell is bound to an antibody 4E3 or 1C10, a labeling of the anti-mouse immunoglobulin antibody is detected, while when not bound, the labeling is not detected. As shown in Table 1, influenza type-A viruses (14 types) isolated from human, and influenza type-A viruses (16 types) and influenza type-B viruses (5 types) each isolated from avian species were used as an influenza virus. The results are shown in Table 1. In Table 1, the case where a binding of an influenza virus which had infected to MDCK cell and an antibody was found therein was represented as "+", and the case where the binding was not found therein was represented as "−".

TABLE 1

| Virus strain | | | 4E3 | 1C10 |
|---|---|---|---|---|
| Influenza type-A | Isolated from human | A/Beijing/262/95(H1N1) | − | − |
| | | A/New Caledonia/20/99(H1N1) | − | − |
| | | A/Bangkok/10/83(H1N1) | − | − |
| | | A/Yamagata/120/86(H1N1) | − | − |
| | | A/Yamagata/32/89(H1N1) | − | − |
| | | A/PR/8/34(H1N1) | − | − |
| | | A/Okuda/57(H2N2) | − | − |
| | | A/Wyoming/3/03(H3N2) | − | − |
| | | A/Aichi/2/68(H3N2) | − | − |
| | | A/Sydney/5/97(H3N2) | − | − |
| | | A/Panama/2007/99(H3N2) | − | − |
| | | A/Fukuoka/C29/85(H3N2) | − | − |
| | | A/Sichuan/2/87(H3N2) | − | − |
| | | A/Kitakyusyu/159/93(H3N2) | − | − |

TABLE 1-continued

| | | Virus strain | 4E3 | 1C10 |
|---|---|---|---|---|
| | Isolated from avian species | A/Budgreiger/Aichi/1/77(H3N8) | + | − |
| | | A/Duck/Czechoslovakia/1/56(H4N6) | + | − |
| | | A/Crow/Kyoto//04(H5N1) | + | + |
| | | A/Duck/HK/342/78(H5N2) | + | + |
| | | A/Duck/HK/820/80(H5N3) | + | + |
| | | A/Turkey/Ontario/7732/66(H5N9) | + | + |
| | | A/Shearwater/Australia/1/72(H6N5) | + | − |
| | | A/Tufted duck/Shimane/124R/80(H7N7) | + | − |
| | | A/Turkey/Ontario/6118/68(H8N4) | + | − |
| | | A/Turkey/Wisconsin/66(H9N2) | + | − |
| | | A/Chicken/Germany/N/49(H10N7) | + | − |
| | | A/Duck/England/56(H11N6) | + | − |
| | | A/Duck/Alberta/60/76(H12N5) | + | − |
| | | A/Gull/Maryland/704/77(H13N6) | + | − |
| | | A/Mallard/Astrakhan/263/82(H14N5) | + | − |
| | | A/Duck/Australia/341/83(H15N8) | + | − |
| Influenza type-B | | B/Lee seed/40 | − | − |
| | | B/Shandong/7/97 | − | − |
| | | B/Yamanashi/166/98 | − | − |
| | | B/Johannesburg/5/99 | − | − |
| | | B/Shanghai/361/02 | − | − |

From the results shown in Table 1, it was confirmed that 4E3 was reactive to influenza type-A viruses subtypes H3 to H15 each isolated from avian species. In addition, it was confirmed that 1C10 was just reactive to only influenza type-A virus subtype H5 isolated from avian species.

Example 1

Using the above-mentioned 4E3 as each of a primary antibody to be labeled with a labeling substance and a secondary antibody to be immobilized on the immunochromatographic membrane carrier 5, the immunochromatographic test tool 1 (hereinafter referred to as "test tool") was manufactured as follows.

First, as shown in FIG. 1, using an antibody applicator (manufactured by BioDot Inc), 4E3 which was diluted with phosphate buffer (pH7.0) so as to have concentration of 2.0 mg/mL was applied onto the judgment region 5A of the immunochromatographic membrane carrier 5 made of a nitrocellulose membrane. Thereafter, the carrier was dried at 50° C. for 30 minutes.

Dried immunochromatographic membrane carrier 5 was soaked in a blocking solution (phosphate buffer (pH7.0) containing BSA), to perform blocking of the carrier. Thereafter, the carrier was washed with washing solution (phosphate buffer (pH7.0) containing SDS) and then dried at 40° C. for 120 minutes, to give an immunochromatographic membrane carrier 5.

Next, 4E3-conjugated latex particle was prepared by contacting 4E3 with blue-colored polystyrene latex particles (particle size of 0.3 μm), and thereafter suspending the resulting products in a suspension buffer (phosphate buffer (pH7.0) containing BSA and sucrose). The concentration of antibodies used in the contact was 200 μg of IgG in 1 mL of 1% latex particle solution. The 4E3-conjugated latex particle was added to a glass fiber pad. Thereafter, the pad was dried in vacuum drier to give a label holding member 4.

Then, using the immunochromatographic membrane carrier 5 and the label holding member 4, the test tool of Example 1 was prepared in the usual manner.

Test Example 1

Using the test tool of Example 1, the reactivity thereof to an influenza virus (human influenza virus) isolated from human was studied.

(1) In this Test Example, as virus fluid were used a dilution obtained by culturing 19 types of human influenza viruses shown in the following Table 2 in a chick-embyonal cultivation, and diluting the resulting viruses with a saline. A virus concentration in a virus fluid was represented as HA value or FFU. Virus concentrations in virus fluids are shown in Table 2. HA value is a unit for a method for quantifying an influenza virus (hemagglutination method) utilizing a hemagglutination activity of an influenza virus, and the criteria showing an activity of an infectious virus. FFU (focus forming unit) is a unit showing the number of viruses calculated on the basis of the number of virus-infected cells which can be confirmed by immunological staining of viruses infected to cells. Here, the symbol "−" in HA value or FFU in Table 2 shows that HA value or FFU is not determined.

(2) Next, to 800 μL of a sample extraction reagent [phosphate buffer (pH7.3) containing 0.3w/v % NP-40 (polyoxyethylene (9) octylphenyl ether)] was added 150 μL of a virus fluid having a given concentration and then mixed, to give a sample.

(3) 200 μL of the sample prepared in (2) was dropped onto a glass test tube. Then, an upstream part of test tool 1 (sample addition member 3) was put therein and thereafter the test tool 1 was left to stand. About 10 minutes later, the coloration in judgment region 5A was observed with the naked eye. In the determination, the case where the coloration was found was evaluated as "+", while the case where the coloration was not found was evaluated as "−". These results are shown in Table 2.

As Comparative Example, a test tool was prepared in the same manner as in Example 1, except for using the above-mentioned 1C10 as a primary antibody and a secondary antibody (Comparative Example 1). In addition, a test tool was prepared in the same manner as in Example 1, except for using 4E3 as a primary antibody, and 1C10 as a secondary antibody (Comparative Example 2).

In addition, POCTEM influenza A/B (manufactured by SYSMEX CORPORATION) which was a commercially available influenza test kit for human was used as Comparative Example 3. The evaluation of the test tools of Comparative Examples 1 to 2 was carried out in the same manner as in the Test Example 1. The evaluation of each of the test tool of Comparative Example 3 was carried out according to a manual attached in the kit. These results are also shown in Table 2.

TABLE 2

| | Virus strain | Comparative Example 1 | Comparative Example 2 | Comparative Example 3 | Example 1 | Concentration tested HA value | Concentration tested FFU/mL |
|---|---|---|---|---|---|---|---|
| H1N1 | A/Beijing/262/95 (H1N1) | – | – | +(A) | – | 85 | — |
| | A/New Caledonia/20/99 (H1N1) | – | – | +(A) | – | — | $1.1 \times 10^7$ |
| | A/Bangkok/10/83 (H1N1) | – | – | +(A) | – | 85 | — |
| | A/Yamagata/120/86 (H1N1) | – | – | +(A) | – | 43 | — |
| | A/Yamagata/32/89 (H1N1) | – | – | +(A) | – | 85 | — |
| | A/PR/8/34 (H1N1) | – | – | +(A) | – | 171 | — |
| H2N2 | A/Okuda/57 (H2N2) | – | – | +(A) | – | 43 | — |
| H3N2 | A/Wyoming/3/03 (H3N2) | – | – | +(A) | – | 85 | $6.3 \times 10^6$ |
| | A/Aichi/2/68 (H3N2) | – | – | +(A) | – | 85 | — |
| | A/Sydney/5/97 (H3N2) | – | – | +(A) | – | — | $1.0 \times 10^7$ |
| | A/Panama/2007/99 (H3N2) | – | – | +(A) | – | — | $3.7 \times 10^6$ |
| | A/Fukuoka/C29/85 (H3N2) | – | – | +(A) | – | 21 | $2.6 \times 10^6$ |
| | A/Sichuan/2/87 (H3N2) | – | – | +(A) | – | 21 | $6.7 \times 10^5$ |
| | A/Kitakyusyu/159/93 (H3N2) | – | – | +(A) | – | 85 | $9.0 \times 10^6$ |
| B型 | B/Lee seed/40 | – | – | +(B) | – | 21 | — |
| | B/Shandong/7/97 | – | – | +(B) | – | 21 | — |
| | B/Yamanashi/166/98 | – | – | +(B) | – | 21 | — |
| | B/Johannesburg/5/99 | – | – | +(B) | – | 21 | — |
| | B/Shanghai/361/02 | – | – | +(B) | – | 43 | — |

From the results shown in Table 2, it was found that all of test tools of Example 1, Comparative Examples 1 and 2 were completely unreactive to influenza viruses (human influenza viruses) isolated from human. On the other hand, that of Comparative Example 3 which was a commercially available influenza test kit for human was reactive to all of human influenza viruses tested.

Test Example 2

Next, it was studied whether or not test tools of Example 1 and Comparative Examples 1 to 3 were reactive to influenza viruses (avian influenza viruses) isolated from avian species.

In this Test Example, as a virus fluid were used a dilution obtained by culturing 17 types of human influenza viruses shown in the following Table 3 in a chick-embyonal cultivation, and diluting the resulting viruses with a saline. Virus concentrations in each of virus fluids are shown in Table 3. Here, in HA values or FFU of Table 3, (–) shows that HA value or FFU is not determined.

From the results shown in Table 3, it was found that the test tool of Example 1 was reactive to all of avian influenza viruses tested (subtypes H3 to H15). On the other hand, the test tools of Comparative Examples 1 and 2 were just reactive to an avian influenza virus subtype H5. The test tool of Comparative Example 3 (commercially available influenza test kit for human) was reactive to all of avian influenza viruses tested.

From the results of Test Examples 1 and 2, since the anti-influenza virus antibody (4E3 or 1C10) was used as a secondary antibody in each of the test tools of Example 1 and Comparative Examples 1 to 2, wherein the antibody was unreactive to human influenza viruses (type A (subtypes H1 to H3) and type B), and was reactive to an avian influenza virus, an avian influenza type-A virus can be detected as distinguishing an avian influenza virus from a human influenza virus, while the conventional test tool (Comparative Example 3) only detected an influenza virus as an influenza type-A virus without distinguishing an avian influenza virus from a human influenza virus. In addition, since 4E3 used in

TABLE 3

| Virus strain | Comparative Example 1 | Comparative Example 2 | Comparative Example 3 | Example 1 | Concentration tested HA value | Concentration tested FFU/mL |
|---|---|---|---|---|---|---|
| A/Budgreiger/Aichi/1/77 (H3N8) | – | – | +(A) | + | 171 | — |
| A/Duck/Czechoslovakia/1/56 (H4N6) | – | – | +(A) | + | 85 | — |
| A/Duck/HK/342/78 (H5N2) | + | + | +(A) | + | — | $1.1 \times 10^7$ |
| A/Turkey/Ontario/7732/66 (H5N9) | + | + | +(A) | + | — | $1.375 \times 10^6$ |
| A/Shearwater/Australia/1/72 (H6N5) | – | – | +(A) | + | 85 | — |
| A/Duck/HK/301/78 (H7N1) | – | – | +(A) | + | 128 | — |
| A/Tufted duck/Shimane/124R/80 (H7N7) | – | – | +(A) | + | 43 | — |
| A/Turkey/Ontario/6118/68 (H8N4) | – | – | +(A) | + | 11 | — |
| A/Turkey/Wisconsin/66 (H9N2) | – | – | +(A) | + | 43 | — |
| A/Duck/HK/448/78 (H9N2) | – | – | +(A) | + | 68 | — |
| A/Duck/HK/702/79 (H9N5) | – | – | +(A) | + | 68 | — |
| A/Chicken/Germany/N/49 (H10N7) | – | – | +(A) | + | 24,016 | — |
| A/Duck/England/56 (H11N6) | – | – | +(A) | + | 171 | — |
| A/Duck/Alberta/60/76 (H12N5) | – | – | +(A) | + | — | $1.1 \times 10^6$ |
| A/Gull/Maryland/704/77 (H13N6) | – | – | +(A) | + | — | $1.1 \times 10^7$ |
| A/Mallard/Astrakhan/263/82 (H14N5) | – | – | +(A) | + | — | $3.1 \times 10^6$ |
| A/Duck/Australia/341/83 (H15N8) | – | – | +(A) | + | — | $2.2 \times 10^6$ |

the test tool of Example 1 is reactive to plural subtypes of avian influenza viruses, the test tool of Example 1 can detect plural subtypes of avian influenza viruses; while the test tools of Comparative Examples 1 to 2 can just detect an avian influenza virus subtype H5. Namely, using the test tool of Example 1, plural subtypes of avian influenza viruses can be detected.

Test Example 3

Using the test tools of Example 1, Comparative Examples 1 and 2, a dilution test was carried out on 2 kinds of viruses belonging to an avian influenza virus subtype H5, to thereby determine the sensitivity of each of test tools.

In this Test Example, as a virus fluid, dilutions each obtained by diluting with a saline each of avian influenza viruses H5N2 (A/Duck/HK/342/78) and H5N9 (A/Turkey/Ontario/7732/66) were used. Concretely, a virus fluid of avian influenza virus H5N2 was prepared as follows: first, a fluid having a virus concentration of $1.1\times10^7$ FFU/mL was prepared. Then, the resulting fluid was diluted in serial dilution, to give virus fluids each having a virus concentration shown in the following Table 4. A virus fluid of an avian influenza virus H5N9 was prepared as follows: first, a fluid having a virus concentration of $1.375\times10^6$ FFU/mL was prepared. Then, the resulting fluid was diluted in serial dilution, to give virus fluids each having a virus concentration shown in the following Table 5. Using the virus fluids, the test was carried out in the same manner as in the above-mentioned Test Example 1. The results for an avian influenza virus H5N2 are shown in Table 4. The results for an avian influenza virus H5N9 are shown in Table 5.

TABLE 4

| | FFU/mL | | | | | | | | |
|---|---|---|---|---|---|---|---|---|---|
| | 11,000,000 | 5,500,000 | 2,750,000 | 1,375,000 | 687,500 | 343,750 | 171,875 | 85,938 | 42,969 |
| Example 1 | + | + | + | + | + | + | − | − | − |
| Comparative Example 1 | + | + | + | − | − | − | − | − | − |
| Comparative Example 2 | + | − | − | − | − | − | − | − | − |

TABLE 5

| | FFU/mL | | | | | | | | |
|---|---|---|---|---|---|---|---|---|---|
| | 1,375,000 | 687,500 | 344,000 | 172,000 | 86,000 | 43,000 | 21,500 | 10,750 | 5,375 |
| Example 1 | + | + | + | + | + | + | + | + | − |
| Comparative Example 1 | + | + | + | + | − | − | − | − | − |
| Comparative Example 2 | + | − | − | − | − | − | − | − | − |

From the results shown in Tables 4 and 5, it was found that an avian influenza virus subtype H5 can be detected more sensitively by the test tool of Example 1 using 4E3 as each of a primary antibody and a secondary antibody, compared to the test tools of Comparative Examples 1 and 2 using 1C10 as a secondary antibody.

Test Example 4

Using the test tool of Example 1, the reactivity thereof to avian influenza virus which infected to human was studied.

In this Test Example, a pharyngeal swab was collected from human infected by any of 10 types of avian influenza viruses shown in the following Table 6. Thereafter, MDCK cell was inoculated with the resulting swab was inoculated and then cultured for 4 to 5 days. After culture, a supernatant of the resulting culture was collected. Using the supernatant as a virus fluid, test was carried out in the same manner as in the above-mentioned Test Example 1. In addition, using the kit of the above-mentioned Comparative Example 3 as Comparative Example, the evaluation thereof was carried out according to a manual attached in the kit. These results are also shown in Table 6.

TABLE 6

| | Comparative Example 3 | | |
|---|---|---|---|
| Virus strain | Flu A | Flu B | Example 1 |
| 1. Flu A/H5 SP/33/04 | + | − | + |
| 2. Flu A/H5 SP/83/04 | + | − | + |
| 3. Flu A/H5 KAN/353/04 | + | − | + |
| 4. Flu A/H5 KK/494/04 | + | − | + |
| 5. Flu A/H5 SP/528/04 | + | − | + |
| 6. Flu A/H5 NKRM/1035/04 | + | − | + |
| 7. Flu A/H5 PCBR/1623/04 | + | − | + |
| 8. Flu A/H5 PCB/2031/04 | + | − | + |

TABLE 6-continued

| | Comparative Example 3 | | |
|---|---|---|---|
| Virus strain | Flu A | Flu B | Example 1 |
| 9. Flu A/H5 SKT/2964/04 | + | − | + |
| 10. Flu A/H5 TH/878/05 | + | − | + |

From the results shown in Table 6, it was found that the test tool of Example 1 can detect avian influenza viruses which infected to human.

Next, in order to study whether or not each of two or more kinds of anti-influenza antibodies can be used as a primary antibody, a test tool of Example 2 was prepared.

Example 2

A test tool of Example 2 was obtained in the same manner as in the above-mentioned Example 1, except for using each of 4E3 and 1C10 in equivalent amounts as a primary antibody.

Test Example 5

Sensitivities of these test tools against avian influenza virus subtype H5 which is different from those used in Test Example 3 was determined by using the test tools of Examples 1 and 2.

In this Test Example, test was carried out in the same manner as in Test Example 3, except for using an avian influenza virus H5N3(A/Duck/HK/820/80) and diluting the virus with a saline so as to have a virus concentration of $3.4\times10^6$ FFU/mL. The results are shown in Table 8. Each of bands was judged by classifying them into any one of 5 levels consisting of "−", "W", "1+", "2+" and "3+" in accordance with a degree of blue colorization. The levels "−", "W", "1+" "2+" and "3+" were set by using the criteria described in Table 7 on the basis of the measured values obtained by measuring the appeared bands with TRS3000 Membrane Strip Reader (manufactured by BioDot corporation). The ROD value in the table is a value calculated by subtracting the value measured for the density of a nitrocellulose membrane as a background from the values measured for those of the bands. Here, blue-colored band can be confirmed with the naked eyes, in the case where the classification is any one of "W", "1+", "2+" and "3+".

TABLE 7

| | ROD value |
|---|---|
| — | 0.000~0.006 |
| W | 0.007~0.014 |
| 1+ | 0.015~0.029 |
| 2+ | 0.030~0.079 |
| 3+ | 0.080 or more |

TABLE 8

| | | | Upper stand: titer (FFU/mL) Lower stand: Dilution ratio | | | |
|---|---|---|---|---|---|---|
| | Primary antibody | Secondary antibody | 425,000 8-fold | 212,500 16-fold | 106,250 32-fold | 53,125 64-fold |
| Example 1 | 4E3 | 4E3 | 2+ | 1+ | W | — |
| Example 2 | 4E3/1C10 | 4E3 | 2+ | W | W | — |

From the results shown in Table 8, it was found that an avian influenza virus can be detected by the test tools of Examples 1 and 2 in the similar sensitivity. From the results, it was found that an avian influenza virus can be also detected by the test tool in which a combination of 4E3 and other anti-influenza virus antibody reactive to an avian influenza virus, as a primary antibody, and 4E3 as a secondary antibody were used. The sensitivity of the test tool of Example 1 is slightly better than that of the test tool of Example 2.

Test Example 6

By an immunoprecipitation method, the antigens recognized by each of monoclonal antibodies 4E3 and 1C10 used in the abovementioned Test Example 5 were identified.

Each of A/Kitakyusyu/159/93 (H3N2) which was an influenza virus subtype H3 and A/Turkey/Ontario/7732/66 (H5N9) which was an influenza virus subtype H5 was used as a virus.

As an antibody, used were the above-mentioned 4E3 and 1C10, an antibody 7304 (manufactured by Medix Biochemica Ab) recognizing a nucleoprotein (NP) of an influenza type-A virus, an antibody 41027 (manufactured by Capricorn Products LLC.) recognizing a nucleoprotein (NP) of an influenza type-B virus, and an antibody F49 (manufactured by TAKARA BIO INC.) recognizing a hemagglutinin (HA) of an influenza type-A virus subtype H3.

1. Viral Infection

Each of confluent MCDK cells in 6 wells was infected with the above-mentioned virus for 1 hour. After removal of the supernatants from the resulting cultures, each 1 mL of isolation media were added to the residuals. The mixtures were cultured over daytime and night. The resulting cells were scraped to collect in tube. After centrifugation, the cells were washed with Cold PBS (−). To the washed cells, a solubilizing solution was added. Then, cells were disrupted by subjecting the resulting mixture to sonication, and thereafter the whole disrupted products were preserved with dry ice.

2. Labeling and Immunoprecipitation

Using Cellular Labeling and Immunoprecipitation kit (manufactured by Roche Diagnostics Corporation), a labeling and an immunoprecipitation were carried out in accordance with manual attached in the kit. First, a viral protein is biotinylated. Thereafter, the biotinylated viral proteins an antibody and a protein A-sepharose are mixed, thereby forming on the protein A-sepharose a complex of the antibody and the biotinylated viral protein bound specifically to the antibody.

3. Electrophoresis

To the above-mentioned sepharose, 50 μL of an electrophoretic buffer was added. The resulting mixture was boiled at 100° C. for 3 minutes. After each 10 μL of samples were applied to a gradient gel (5 to 20%), an electrophoresis (SDS-PAGE) was carried out at 30 mA for 90 minutes. Proteins on the gel after electrophoresis were transferred at 250 mA for 2 hours into PVDF membrane. Thereafter, the membrane was blocked with 5% skim milk·PBS(−) and then washed three times. The membrane was reacted with a streptavidin-POD solution diluted in 1:1000 for 30 minutes, and then washed. Detection was carried out by using 4-chloronaphtathol solution. The results are shown in FIG. 2.

Figure 2:
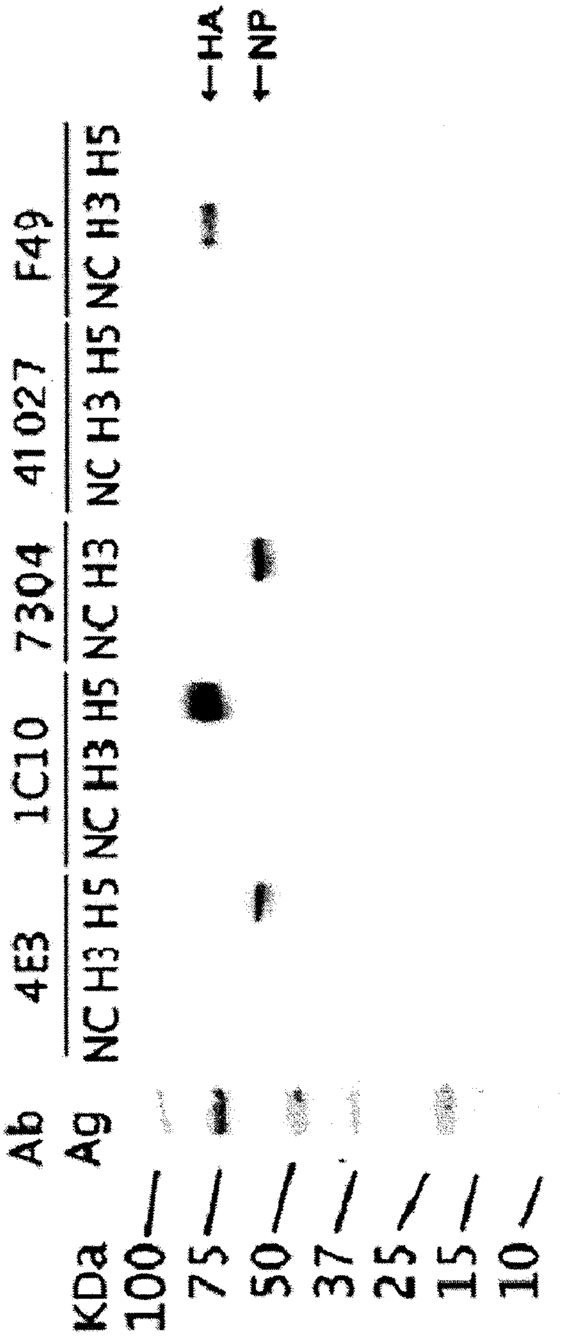
FIG. 2 is a diagram of the results of a test for identifying an antigen which is recognized by each of a monoclonal antibody 4E3 and 1C10.

From the results shown in FIG. 2, since a band appeared in the lane for virus H5 of the lanes for 4E3 was presented at the same mobility position of a band appeared in the lane for 7304 (antibody recognizing a nucleoprotein (NP) of an influenza type-A), it was found that the 4E3 was an antibody recognizing a nucleoprotein (NP) of an avian influenza virus (H5N9). In addition, the band appeared in the lane for H5 virus of the lanes for 1C10 was presented at the same mobility position of a band appeared in the lane for F49, it was found that the 1C10 was an antibody recognizing hemagglutinin (HA) of an avian influenza virus (H5N9).

Test Example 7

For the purpose of identifying an epitope which is recognized by the monoclonal antibody 4E3 used in the above Test Example 5, the following experiments were carried out.

(1) Preparation of a Recombinant Nucleoprotein (NP)

MDCK cells were infected with a human influenza virus strain (Puerto Rico/8/34) which obtained from Osaka Prefectural Institute of Public Health as human influenza virus, and thereafter the infected MDCK cells were cultured. Viral nucleic acids were extracted from the resulting conditioned medium by using QIAGEN Magtration system 6GC (manufactured by QIAGEN Inc.) and EZ Virus Mini Kit reagent (manufactured by QIAGEN Inc.). Then, a DNA fragment containing a region encoding a human influenza virus NP was amplified from the extracted viral nucleic acid by RT-PCR method using the following primers (SEQ ID NOs: 1 and 2).

```
Forward primer:
5'-ATGGCGTCCCAAGGCACCAA-3'        (SEQ ID NO: 1)

Reverse primer:
5'-TTAATTGTCGTACTCCTCTGCA-3'      (SEQ ID NO: 2)
```

In order to add cleavage sites for restriction enzymes (KpnI and EcoRI) and a sequence encoding 6 histidine residues to the DNA fragment amplified in the above containing a region encoding a human influenza virus NP, PCR was carried out by using the following primer (SEQ ID NOs: 3 and 4).

```
Forward primer:
                                    (SEQ ID NO: 3)
5'-ATGGTACCATGGCGTCCCAAGGCACCAA-3'

Reverse primer:
                                    (SEQ ID NO: 4)
5'-TAGAATTCTAGTGATGGTGATGGTGATGATTGTCGTACTCCTCTGCA
TT-3'
```

Therefore, the recombinant NP obtained in this Test Example has addition of 6 histidine residues at C-terminal.

Cultured were cells infected with the avian influenza virus strain (H5N9/Ontario/7732/1966) obtained from Osaka Prefectural Institute of Public Health. Thereafter, viral nucleic acids were extracted in the same manner as in the above from the resulting conditioned medium. Next, a DNA fragment containing a region encoding an avian influenza virus NP was amplified from the extracted viral nucleic acids by RT-PCR method using the following primers (SEQ ID NOs:5 and 6).

```
Forward primer:
5'-ATGGCGTCTCAAGGCACCAAAC-3'      (SEQ ID NO: 5)

Reverse primer:
5'-TTAATTGTCATATTCCTCTGCATTG-3'   (SEQ ID NO: 6)
```

In order to add a sequence of cleavage sites for restriction enzymes (KpnI and EcoRI) and a sequence encoding 6 histidine residues to the amplified DNA fragment containing the region encoding the avian influenza virus NP, PCR was carried out by using the following primers (SEQ ID NOs:7 and 8).

```
Forward primer:
                                    (SEQ ID NO: 7)
5'-ATGGTACCATGGCGTCTCAAGGCACCAAAC-3'

Reverse primer:
                                    (SEQ ID NO: 8)
5'-TAGAATTCTAGTGATGGTGATGGTGATGATTGTCATATTCCTCTGCA
TTGTC-3'
```

Each of the resulting DNA fragments (each containing restriction enzyme cleavage sites and sequence encoding 6 histidine residues) was inserted into KpnI/EcoRI sites in pcDNA3.1(+) (manufactured by Invitrogen Corporation), which is the NP expression vector for eukaryotic cell, to thereby prepare a wild-type human influenza NP expression vector and a wild-type avian influenza NP expression vector.

Next, the wild-type human influenza NP expression vector was digested with restriction enzymes (KpnI and BamHI). After electrophoresis of the resulting fragments, a DNA fragment encoding N-terminal 159 amino acids of the human influenza NP and a fragment encoding C-terminal 339 amino acids of the NP, 6 histidine residues and vector were purified by using QIAquick Gel Extraction Kit (manufactured by QIAGEN Inc.).

In the same way in the above, the wild-type avian influenza NP expression vector was subjected to a treatment with restriction enzymes (KpnI and BamHI). After electrophoresis of the resulting fragments, a DNA fragment encoding N-terminal 159 amino acids of the avian influenza NP and a fragment encoding C-terminal 339 amino acids of the NP, 6 histidine residues and vector were purified.

Using DNA ligation kit (manufactured by TAKARA BIO INC.), a chimeric NP1 expression vector was constructed by ligating the DNA fragment encoding N-terminal 159 amino acids of the avian influenza NP and the fragment encoding C-terminal 339 amino acids of the human influenza NP, 6 histidine residues and vector.

In the same way as in the above, a chimeric NP2 expression vector was constructed by ligating a DNA fragment encoding N-terminal 159 amino acids of the human influenza NP and a fragment encoding C-terminal 339 amino acids of the avian influenza NP, 6 histidine residues and vector.

Next, the wild-type human influenza NP expression vector was digested with restriction enzymes (KpnI and ApaLI). Thereafter, a DNA fragment encoding N-terminal 45 amino acids of the human influenza NP and a fragment encoding C-terminal 453 amino acids of the NP, 6 histidine residues and vector were purified in the same manner as in the above.

In addition, the wild-type avian influenza NP expression vector was digested with restriction enzymes (KpnI and ApaLI). Thereafter, a DNA fragment encoding N-terminal 45 amino acids of the avian influenza NP and a fragment encoding C-terminal 453 amino acids of the NP, 6 histidine residues and vector were purified in the same manner as in the above.

Using DNA Ligation kit (manufactured by TAKARA BIO INC.), a chimeric NP3 expression vector was constructed by ligating the DNA fragment encoding N-terminal 45 amino acids of the avian influenza NP and the fragment encoding C-terminal 453 amino acids of the human influenza NP, 6 histidine residues and vector.

In the same manner, a chimeric NP4 expression vector was constructed by ligating the DNA fragment encoding N-terminal 45 amino acids of the human influenza NP and a fragment encoding C-terminal 453 amino acids of the avian influenza NP, 6 histidine residues and vector.

Each of the wild-type human influenza NP expression vector, the wild-type avian influenza NP expression vector, the chimeric NP1 expression vector, the chimeric NP2 expression vector, the chimeric NP3 expression vector and the chimeric NP4 expression vector prepared in the above was purified by using EndoFree Plasmid Maxi Kit (manufactured by QIAGEN Inc.). Then, each of the expression vectors purified was introduced into a COS-7 cell derived from a simian kidney by using Superfect transfection reagent (manufactured by QIAGEN Inc.). The resulting cells were incubated for 48 hours in an incubator at 5% $CO_2$, to express each of recombinant NPs. Among them, a recombinant NP obtained from the wild-type human influenza NP expression vector was named as r-Human Flu NP (SEQ ID NO: 9), a recombinant NP obtained from the wild-type avian influenza NP expression vector being as r-Avian Flu NP (SEQ ID NO:10), a recombinant NP obtained from the chimeric NP1 expression vector being as r-Ch1 Flu NP (SEQ ID NO: 11), a recombinant NP obtained from the chimeric NP2 expression vector being as r-Ch2 Flu NP (SEQ ID NO: 12), a recombinant NP obtained from the chimeric NP3 expression vector being as r-Ch3 Flu NP (SEQ ID NO: 13), and a recombinant NP obtained from chimeric NP4 expression vector being as r-Ch4 Flu NP (SEQ ID NO: 14).

Figure 3:
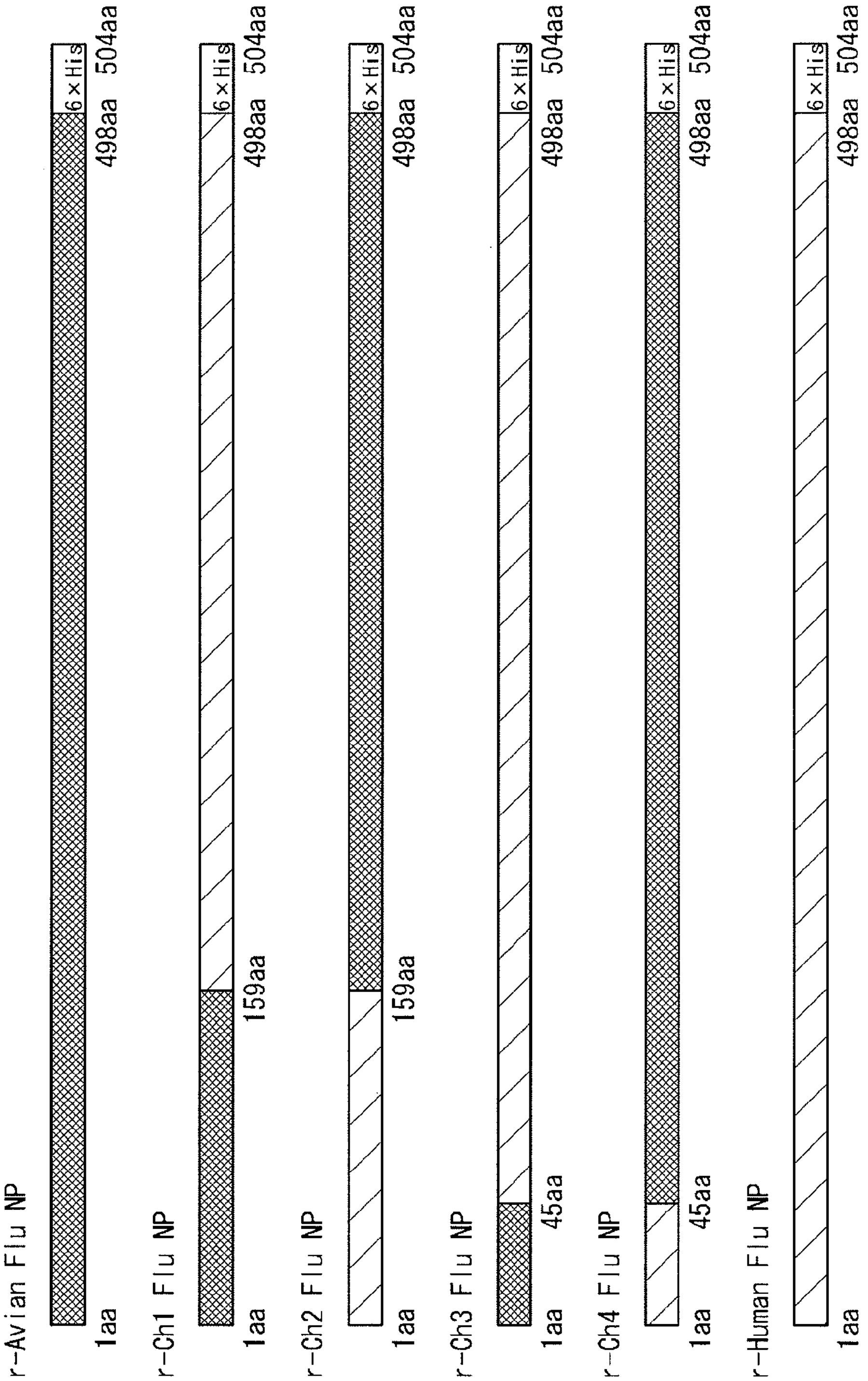
FIG. 3 is a schematic diagram showing amino acid sequences of r-Human Flu NP(SEQ ID NO:9), r-Avian Flu NP(SEQ ID NO:10), r-Ch1 Flu NP(SEQ ID NO:11), r-Ch2 Flu NP(SEQ ID NO:12), r-Ch3 Flu NP(SEQ ID NO:13), and r-Ch4 Flu NP (SEQ ID NO:14)

FIG. 3 is a schematic diagram showing amino acid sequences of r-Human Flu NP (SEQ ID NO: 9), r-Avian Flu NP (SEQ ID NO: 10), r-Ch1 Flu NP (SEQ ID NO: 11), r-Ch2 Flu NP (SEQ ID NO: 12), r-Ch3 Flu NP (SEQ ID NO: 13) and r-Ch4 Flu NP (SEQ ID NO: 14). A shown in FIG. 3, all of amino acid sequences has 504 residues in length, of which C-terminal 6 amino acid residues (namely, amino acid sequence at positions 499 to 504) were histidines.

In addition, an amino acid sequence at positions 1 to 498 of r-Human Flu NP corresponds to a full-length amino acid sequence (498 residues) of the human influenza virus NP.

An amino acid sequence at positions 1 to 498 of r-Avian Flu NP corresponds to a full-length amino acid sequence (498 residues) of the avian influenza virus NP.

An amino acid sequence at positions 1 to 159 of r-Ch1 Flu NP corresponds to N-terminal 159 amino acids of the avian influenza NP, and an amino acid sequence at positions 160 to 498 corresponds to C-terminal 339 amino acids of the human influenza NP.

An amino acid sequence at positions 1 to 159 of r-Ch2 Flu NP corresponds to N-terminal 159 amino acids of the human influenza NP, and an amino acid sequence at positions 160 to 498 corresponds to C-terminal 339 amino acids of the avian influenza NP.

An amino acid sequence at positions 1 to 45 of r-Ch3 Flu NP corresponds to N-terminal 45 amino acids of the avian influenza NP, and an amino acid sequence at positions 46 to 498 corresponds to C-terminal 453 amino acids of the human influenza NP.

An amino acid sequence at positions 1 to 45 of r-Ch4 Flu NP corresponds to N-terminal 45 amino acids of the human influenza NP, and an amino acid sequence at positions 46 to 498 corresponds to C-terminal 453 amino acids of the avian influenza NP. For reference, amino acid sequences of r-Human Flu NP and r-Avian Flu NP prepared in the above, NPs derived from 12 types of human influenza virus strains described in the below and NPs derived from 12 types of avian influenza virus strains described in the below were shown in FIGS. 4 to 13.

Human Influenza Viruses:

A/HongKong/117/1977(H1N1)
A/Japan/170/62(H2N2)
A/Kitakyushu/159/93(H3N2)
A/Kumamoto/1/65(H2N2)
A/NewYork/5/2004(H3N2)
A/PuertoRico/8/34(H1N1)
A/Kiev/59/79(H1N1)
A/Beijing/353/1989(H3N2)
A/Brazil/11/1978(H1N1)
A/Victoria/15681/59(H2N2)
A/NewCaledonia/20/1999(H1N1)
A/Panama/2007/1999(H3N2)

Avian Influenza Viruses:

A/Duck/Australia/341/83(H15N8)
A/Mallard/Astrakan/263/82(H14N8)
A/gull/Maryland/704/1977(H13N6)
A/pintail/Alberta/49/2003(H12N5)
A/duck/England/1956(H11N6)
A/pintailduck/ALB/584/1984(H10N6)
A/shorebird/DE/261/2003(H9N5)
A/turkey/Ontario/6118/1968(H8N4)
A/chicken/Germany/R28/03(H7N7)
A/shearwater/Australia/1972(H6N5)
A/blackduck/NewYork/184/1988(H5N2)
A/turkey/Ontario/7732/1966(H5N9)

(2) Comparison of the Reactivities

Each COS-7 cell expressing the recombinant NP prepared in the (1) was stripped from a dish by using Trypsin-EDTA solution (manufactured by Sigma-Aldrich Co.), and then washed with PBS. Each COS-7 cell after washing was suspended in an appropriate amount of PBS, to give a cell suspension. An appropriate amount of the cell suspension was spotted onto a slide glass, and dried in air. Thereafter the cells were fixed with acetone. To the slide glass after fixation with acetone, a 4E3 antibody solution (PBS containing 10 μg/ml 4E3 and 1% BSA) was dropped, thereby reacting COS-7 cells on the slide glass with 4E3. Next, FITC-labeled anti-mouse Ig antibody (manufactured by Dako Inc.) diluted in 100-fold with PBS containing 1% BSA was dropped onto the slide glass. Then, the reactivities of 4E3 to each of recombinant NPs expressed in COS-7 cells were determined by observing the slide glass under the fluorescence microscope.

Here, as a control, instead of 4E3, an anti-His tag antibody (PentaHis, manufactured by QIAGEN Inc.) was used. The results are shown in FIG. 14.

Figure 14:
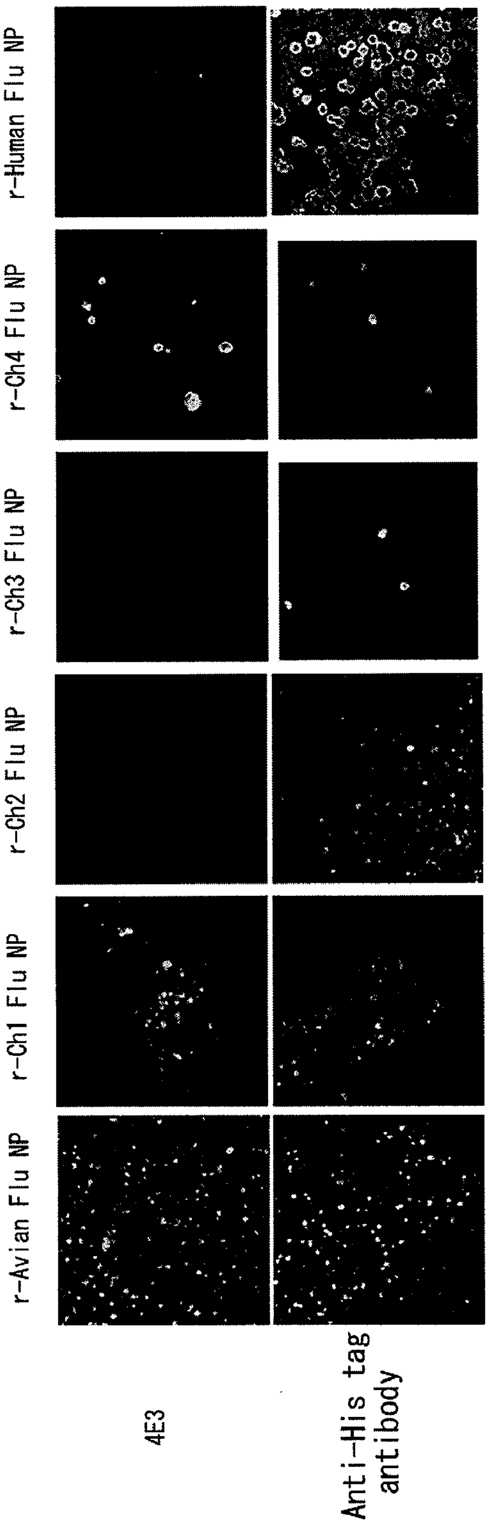
FIG. 14 is a view showing a comparison between the reactivities of 4E3 and an anti-His tag antibody to each of recombinant NPs.

From the results shown in FIG. 14, it was found that 4E3 was unreactive to r-Human Flu NP, r-Ch2 Flu NP and r-Ch3 Flu NP, and was reactive to r-Avian Flu NP, r-Ch1 Flu NP and r-Ch4 Flu NP. Namely, it was found that 4E3 was reactive to a nucleoprotein containing an amino acid sequence at positions 46 to 159 of the avian influenza virus NP, but not reactive to nucleoprotein not containing the sequence. From the results, it can be deduced that 4E3 recognizes an epitope localized in a certain region (an amino acid sequence at positions 46 to 159) of N-terminal side of the avian influenza virus NP.

According to the present invention, an avian influenza virus can be detected specifically, rapidly and in a simple manner as distinguishing and an avian influenza virus from a human influenza virus

The invention claimed is:

1. A method for detecting an avian influenza virus, comprising the step of detecting an avian influenza virus in a sample by an immunological assay, with the use of an anti-influenza virus monoclonal antibody produced by hybridoma 4E3 (Accession No. FERM BP-10904).

2. The method according to claim 1, wherein said immunological assay comprises the step of using a primary antibody against an influenza virus and a secondary antibody against the influenza virus, to form a complex containing a labeled antibody of said primary antibody, said secondary antibody immobilized on a solid phase and said influenza virus, and wherein at least said secondary antibody is the anti-influenza virus monoclonal antibody produced by hybridoma 4E3 (Accession No. FERM BP-10904.

3. The method according to claim 2, wherein each of said primary antibody and secondary antibody is the anti-influenza virus monoclonal antibody produced by hybridoma 4E3 (Accession No. FERM BP-10904).

4. The method according to claim 2, wherein said immunological assay is an immunochromatography.

5. The method according to claim 4, wherein said immunochromatography comprises the step of forming the complex containing the secondary antibody, the labeled primary antibody and the influenza virus on an immunochromatographic membrane carrier having the secondary antibody immobilized thereon.

6. An immunochromatographic test tool for detecting an avian influenza virus in a sample by utilizing a primary antibody against an influenza virus and a second antibody against an influenza virus, comprising:

a sample addition member to which the sample is applied;

a label holding member in which a primary antibody labeled with labeling substance is hold; and an immunochromatographic membrane carrier having a judgment region placed thereon, said judgment region having the secondary antibody immobilized thereon;

wherein said primary antibody is an anti-influenza virus antibody being reactive to an avian influenza virus, and wherein said secondary antibody is an anti-influenza virus monoclonal antibody produced by hybridoma 4E3 (accession no. FERM BP-10904).

7. The immunochromatographic test tool according to claim 6, wherein said labeling substance is an insoluble granular maker.

8. The immunochromatographic test tool according to claim 7, wherein said insoluble granular maker is a colored synthetic polymer particle or a colloidal metallic particle.

9. The method according to claim 3, wherein said immunological assay is an immunochromatography.

10. The method according to claim 9, wherein said immunochromatography comprises the step of forming the complex containing the secondary antibody, the labeled primary antibody and the influenza virus on an immunochromatographic membrane carrier having the secondary antibody immobilized thereon.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
```

<223> OTHER INFORMATION: designed DNA based on Human influenza virus

<400> SEQUENCE: 1
atggcgtccc aaggcaccaa 20

<210> SEQ ID NO 2
<211> LENGTH: 22
<212> TYPE: DNA
<213> ORGANISM: Artificial Sequence
<220> FEATURE:
<223> OTHER INFORMATION: designed DNA based on Human influenza virus

<400> SEQUENCE: 2
ttaattgtcg tactcctctg ca 22

<210> SEQ ID NO 3
<211> LENGTH: 28
<212> TYPE: DNA
<213> ORGANISM: Artificial Sequence
<220> FEATURE:
<223> OTHER INFORMATION: designed DNA based on Human influenza virus

<400> SEQUENCE: 3
atggtaccat ggcgtcccaa ggcaccaa 28

<210> SEQ ID NO 4
<211> LENGTH: 49
<212> TYPE: DNA
<213> ORGANISM: Artificial Sequence
<220> FEATURE:
<223> OTHER INFORMATION: designed DNA based on Human influenza virus

<400> SEQUENCE: 4
tagaattcta gtgatggtga tggtgatgat tgtcgtactc ctctgcatt 49

<210> SEQ ID NO 5
<211> LENGTH: 22
<212> TYPE: DNA
<213> ORGANISM: Artificial Sequence
<220> FEATURE:
<223> OTHER INFORMATION: designed DNA based on Avian influenza virus

<400> SEQUENCE: 5
atggcgtctc aaggcaccaa ac 22

<210> SEQ ID NO 6
<211> LENGTH: 25
<212> TYPE: DNA
<213> ORGANISM: Artificial Sequence
<220> FEATURE:
<223> OTHER INFORMATION: designed DNA based on Avian influenza virus

<400> SEQUENCE: 6
ttaattgtca tattcctctg cattg 25

<210> SEQ ID NO 7
<211> LENGTH: 30
<212> TYPE: DNA
<213> ORGANISM: Artificial Sequence
<220> FEATURE:
<223> OTHER INFORMATION: designed DNA based on Avian influenza virus

<400> SEQUENCE: 7
atggtaccat ggcgtctcaa ggcaccaaac 30

<210> SEQ ID NO 8

-continued

```
<211> LENGTH: 52
<212> TYPE: DNA
<213> ORGANISM: Artificial Sequence
<220> FEATURE:
<223> OTHER INFORMATION: designed DNA based on Avian influenza virus

<400> SEQUENCE: 8

tagaattcta gtgatggtga tggtgatgat tgtcatattc ctctgcattg tc            52


<210> SEQ ID NO 9
<211> LENGTH: 504
<212> TYPE: PRT
<213> ORGANISM: Artificial Sequence
<220> FEATURE:
<223> OTHER INFORMATION: Amino acid sequence of r-Human Flu NP

<400> SEQUENCE: 9

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320
```

```
Asn Pro Ala His Lys Ser Gln Leu Val Trp Met Ala Cys His Ser Ala
            325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Lys
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn His His His His His His
            500


<210> SEQ ID NO 10
<211> LENGTH: 504
<212> TYPE: PRT
<213> ORGANISM: Artificial Sequence
<220> FEATURE:
<223> OTHER INFORMATION: Amino acid sequence of r-Avian Flu NP

<400> SEQUENCE: 10

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asn
        115                 120                 125

Ala Ala Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
```

-continued

```
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Ser Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Lys Met Met
        435                 440                 445

Glu Asn Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn His His His His His His
            500
```

<210> SEQ ID NO 11
<211> LENGTH: 504
<212> TYPE: PRT
<213> ORGANISM: Artificial Sequence
<220> FEATURE:
<223> OTHER INFORMATION: Amino acid sequence of r-Ch1 Flu NP

<400> SEQUENCE: 11

```
Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45
```

```
Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asn
        115                 120                 125

Ala Ala Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Lys
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
```

```
465                 470                 475                 480

Met Ser Asn Glu Gly Ser Tyr Phe Phe Gly Asp Asn Ala Glu Glu Tyr
                485                 490                 495

Asp Asn His His His His His His
            500


<210> SEQ ID NO 12
<211> LENGTH: 504
<212> TYPE: PRT
<213> ORGANISM: Artificial Sequence
<220> FEATURE:
<223> OTHER INFORMATION: Amino acid sequence of r-Ch2 Flu NP

<400> SEQUENCE: 12

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Ser Asn Glu
305                 310                 315                 320

Asn Pro Ala His Lys Ser Gln Leu Val Trp Met Ala Cys His Ser Ala
                325                 330                 335
```

-continued

```
Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Lys Met Met
        435                 440                 445

Glu Asn Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn His His His His His His
            500


<210> SEQ ID NO 13
<211> LENGTH: 504
<212> TYPE: PRT
<213> ORGANISM: Artificial Sequence
<220> FEATURE:
<223> OTHER INFORMATION: Amino acid sequence of r-Ch3 Flu NP

<400> SEQUENCE: 13

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190
```

```
Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Lys
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn His His His His His His
            500


<210> SEQ ID NO 14
<211> LENGTH: 504
<212> TYPE: PRT
<213> ORGANISM: Artificial Sequence
<220> FEATURE:
<223> OTHER INFORMATION: Amino acid sequence of r-Ch4 Flu NP

<400> SEQUENCE: 14

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
```

-continued

```
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asn
        115                 120                 125

Ala Ala Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Ser Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Lys Met Met
        435                 440                 445

Glu Asn Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480
```

-continued

```
Met Ser Asn Glu Gly Ser Tyr Phe Phe Gly Asp Asn Ala Glu Glu Tyr
            485                 490                 495

Asp Asn His His His His His His
            500
```